(12) United States Patent
Kubo et al.

(10) Patent No.:   US 12,569,249 B2
(45) Date of Patent:       Mar. 10, 2026

(54) MEDICAL STAPLER

(71) Applicant: OLYMPUS CORPORATION, Tokyo (JP)

(72) Inventors: Ryu Kubo, Hachioji (JP); Takashi Nakamura, Omiya (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 18/969,746

(22) Filed: Dec. 5, 2024

(65) Prior Publication Data

US 2025/0090170 A1     Mar. 20, 2025

Related U.S. Application Data

(63) Continuation      of      application      No. PCT/JP2022/024772, filed on Jun. 21, 2022.

(51) Int. Cl.
A61B 17/10        (2006.01)
A61B 17/00        (2006.01)
A61B 90/00        (2016.01)

(52) U.S. Cl.
CPC ...... *A61B 17/105* (2013.01); *A61B 17/00234* (2013.01); *A61B 90/03* (2016.02); *A61B 2017/00296* (2013.01); *A61B 2090/064* (2016.02)

(58) Field of Classification Search
CPC .. A61B 17/105; A61B 17/00234; A61B 90/03
See application file for complete search history.

(56) References Cited

U.S. PATENT DOCUMENTS 5,395,030 A  *  3/1995  Kuramoto ........ A61B 17/00234
                                                            227/19
8,820,608 B2     9/2014  Miyamoto
                      (Continued)

FOREIGN PATENT DOCUMENTS

EP          0910289 B1       3/2006
JP      2000512185 A       9/2000
                      (Continued)

OTHER PUBLICATIONS

"International Application No. PCT/JP2022/024772, International Search Report dated Aug. 2, 2022", w/ English Translation, (Aug. 2, 2022), 4 pgs.

*Primary Examiner* — Nathaniel C Chukwurah
(74) *Attorney, Agent, or Firm* — Schwegman Lundberg & Woessner. P.A.

(57)                    ABSTRACT
A medical stapler is a medical stapler used together with an endoscope and includes a flexible elongated member extending in a length direction of the endoscope, a wire inserted inside the elongated member and movable forward and backward with respect to the elongated member, a suture assembly connected to a distal end of the wire and being able to suture a gripped treatment target with a staple, an operation unit connected to a rear end of the wire and ejecting the staple from the suture assembly by moving the wire forward and backward, and an ejection restriction structure restricting ejection of the staple when a tension applied to the wire is equal to or less than a first tension caused by a change in shape of the elongated member.

9 Claims, 34 Drawing Sheets

(56)                    References Cited

U.S. PATENT DOCUMENTS

| | | | |
|---|---|---|---|
| 2007/0213743 A1* | 9/2007 | McGuckin, Jr. ............................ | |
| | | | A61B 17/07207 |
| | | | 606/139 |
| 2010/0036396 A1 | 2/2010 | Iida et al. | |
| 2020/0275925 A1 | 9/2020 | Smith et al. | |

FOREIGN PATENT DOCUMENTS

| | | | |
|---|---|---|---|
| JP | 2006116356 A | 5/2006 | |
| JP | 2010035853 A | 2/2010 | |
| JP | 2022522470 A | 4/2022 | |
| WO | WO-2013073523 A1 | 5/2013 | |

\* cited by examiner

MEDICAL STAPLER

The present invention relates to a medical stapler. This application is a continuation application based on International Patent Application No. PCT/JP2022/024772 filed on Jun. 21, 2022, and the content of the PCT international application is incorporated herein by reference.

TECHNICAL FIELD

Background Art

In recent years, a flexible stapler with a suturing mechanism supported by a flexible endoscope has been used in surgery that enables suturing inside a lumen. When a flexible stapler is used, a needle (hereinafter, a staple) is loaded into the suturing mechanism, then is inserted into a lumen, and an affected area is sutured by ejecting the staple once the affected area is accessed. In such a flexible stapler, there is a likelihood that a staple loaded in the suturing mechanism may fall off at an unintended time. For example, if a path length of the wire changes due to a shape of the flexible endoscope, a pulling force generated on the wire may cause the staple to fall off when the suturing mechanism is activated. If the staple falls off within a lumen, the staple remains inside the body and is difficult to remove. Also, the time and effort for removing the flexible stapler from the body to reload the stapler are required, and there is a concern that the procedure time will increase.

As a conventional surgical suturing device, there is one having a configuration in which a suturing mechanism is supported by a rigid shaft (for example, see Patent Document 1). The suturing mechanism described in Patent Document 1 has a locking mechanism for preventing a needle (staple) from unintentionally falling out of a jaw element.

CITATION LIST

Patent Document

[Patent Document 1] Japanese Unexamined Patent Application, First Publication No. 2006-116356

SUMMARY OF INVENTION

Technical Problem

When the above-described locking mechanism is applied to a flexible stapler, movement of the wire connected to the suturing mechanism within a flexible member may be hindered, making it difficult to change a shape of the flexible member and reducing ease of insertion into the lumen or the like.

Therefore, a suturing mechanism capable of curbing unintended falling off of a staple without decreasing ease of insertion into a lumen is desired.

In view of the above circumstances, an objective of the present invention is to provide a suturing mechanism capable of curbing unintended falling off of a staple without decreasing ease of insertion into a lumen, and a medical system including the suturing mechanism.

Solution to Problem

In order to solve the above problems, the present invention proposes the following means.

A medical stapler according to a first aspect of the present invention is a medical stapler used together with an endoscope and includes a flexible elongated member extending in a length direction of the endoscope, a wire inserted inside the elongated member and movable forward and backward with respect to the elongated member, a suture assembly connected to a distal end of the wire and being able to suture a gripped treatment target with a staple, an operation unit connected to a rear end of the wire and ejecting the staple from the suture assembly by moving the wire forward and backward, and an ejection restriction structure restricting ejection of the staple when a tension applied to the wire is equal to or less than a first tension caused by a change in shape of the elongated member.

Advantageous Effects of Invention

The medical stapler of the present invention can curb unintended falling off of a staple without decreasing ease of insertion into a lumen.

DESCRIPTION OF EMBODIMENTS

First, a basic configuration and a method of use of a medical system 300 of the present invention will be described.

[Medical System 300]

Figure 1:
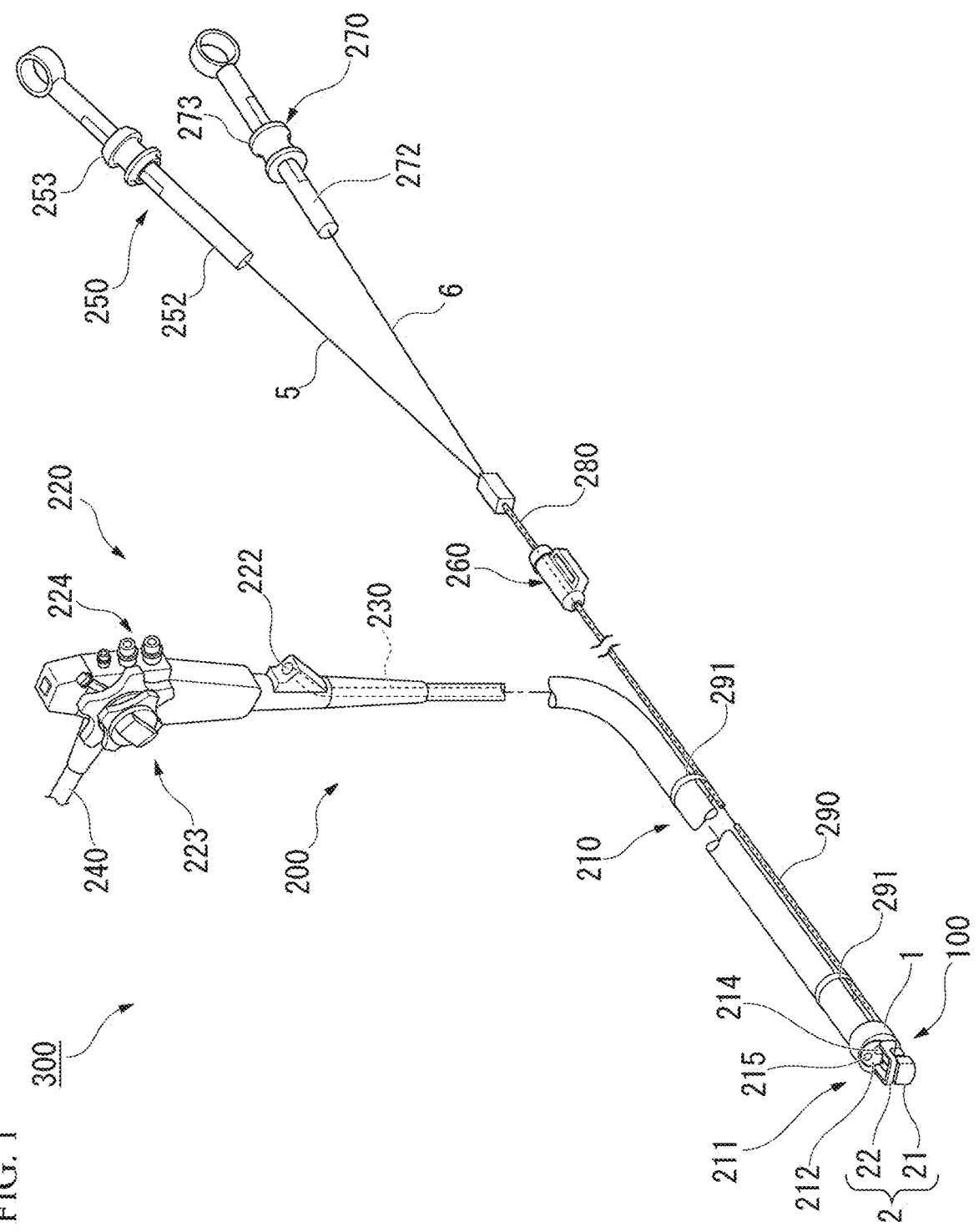
FIG. 1 is a view illustrating an overall configuration of a medical system 300 including a medical stapler 100 according to the present invention.

FIG. 1 is a view illustrating an overall configuration of the medical system 300 including a medical stapler 100 according to the present invention.

The medical system 300 is used for surgery or the like in which the digestive tract or the like is sutured. The medical system 300 includes the medical stapler 100, an endoscope 200, an opening/closing operation unit 250, an ejection operation unit 270, a wire sheath 280, a resin sheath (elongated member) 290, and a wire sheath operation unit 260. The opening/closing operation unit 250 is an operation unit that operates the medical stapler 100 using an opening/closing operation wire 5. The ejection operation unit 270 is an operation unit that operates the medical stapler 100 using an ejection operation wire (wire) 6.

[Endoscope 200]

The endoscope 200 is a known flexible endoscope, and includes a long insertion part 210 that is inserted into the body from a distal end thereof, an operation unit 220 provided at a proximal end part of the insertion part 210, and a universal cord 240.

A treatment tool channel 230 through which an endoscopic treatment tool is inserted is formed in the insertion part 210. A forceps port 214, which is a distal end opening of the treatment tool channel 230, is provided at a distal end 212 of the insertion part 210. The treatment tool channel 230 extends from the distal end 212 of the insertion part 210 to the operation unit 220.

A distal end part 211 of the insertion part 210 includes an imaging unit (not illustrated) including a CCD or the like. An objective lens 215 of the imaging unit is exposed at the distal end 212 of the insertion part 210. The distal end part 211 of the insertion part 210 has a hard portion 211a on a distal end side.

A knob 223 for operating the insertion part 210 and a switch 224 for operating the imaging unit and the like are provided on a proximal end side of the operation unit 220. An operator can bend the insertion part 210 in a desired direction by operating the knob 223.

A forceps insertion port 222 communicating with the treatment tool channel 230 is provided on a distal end side of the operation unit 220. The operator can insert the endoscopic treatment tool into the treatment tool channel 230 through the forceps insertion port 222.

The universal cord 240 connects the operation unit 220 and an external peripheral device. The universal code 240 outputs, for example, an image captured by the imaging unit to an external device. The image captured by the imaging unit is displayed on a display device such as a liquid crystal display via an image processing device.

[Opening/Closing Operation Unit 250]

The opening/closing operation unit 250 is an operation unit that opens and closes the medical stapler 100 by operating the opening/closing operation wire 5. As illustrated in FIG. 1, the opening/closing operation unit 250 includes an opening/closing operation unit main body 252 and an opening/closing operation slider 253. A proximal end of the opening/closing operation wire 5 is connected to the opening/closing operation slider 253. The operator can move the opening/closing operation wire 5 forward and backward by moving the opening/closing operation slider 253 forward and backward in a longitudinal axis direction with respect to the opening/closing operation unit main body 252.

[Ejection Operation Unit 270]

The ejection operation unit 270 is an operation unit that ejects a staple S from the medical stapler 100 by operating the ejection operation wire 6. As illustrated in FIG. 1, the ejection operation unit 270 includes an ejection operation unit main body 272 and an ejection operation slider 273. A proximal end of the ejection operation wire 6 is connected to the ejection operation slider 273. The operator can move the ejection operation wire 6 forward and backward by moving the ejection operation slider 273 forward and backward in a longitudinal axis direction with respect to the ejection operation unit main body 272.

[Wire Sheath 280]

The wire sheath 280 is a sheath through which the opening/closing operation wire 5 and the ejection operation wire 6 are inserted. The wire sheath 280 is a metal coil sheath. Further, the wire sheath 280 is not limited to a metal coil sheath, and may be a sheath of other types.

Two inner sheaths 282 (see FIG. 14) are inserted into the wire sheath 280. The opening/closing operation wire 5 and the ejection operation wire 6 are inserted into the two inner sheaths 282, respectively. Further, the two inner sheaths 282 may be a multi-lumen tube having two lumens.

[Resin Sheath 290]

The resin sheath 290 is a sheath through which the wire sheath 280 is inserted to be movable forward and backward. The resin sheath 290 is formed of resin material. As illustrated in FIG. 1, a distal end side of the resin sheath 290 is connected to the insertion part 210 of the endoscope 200 by a band 291. In the resin sheath 290, a distal end is fixed to a cap 1 of the medical stapler 100 and a proximal end is fixed to the wire sheath operation unit 260.

[Wire Sheath Operation Unit 260]

Figure 2:
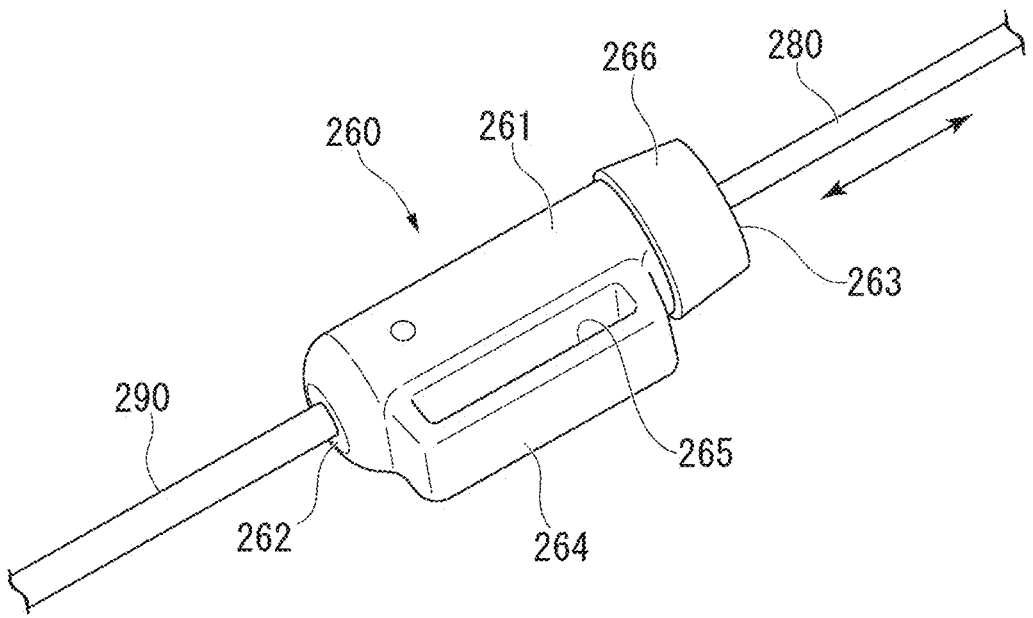
FIG. 2 is a perspective view of a wire sheath operation unit 260.

FIG. 2 is a perspective view of the wire sheath operation unit 260.

The wire sheath operation unit 260 is an operation unit that moves the wire sheath 280 forward and backward with respect to the resin sheath 290. The wire sheath operation unit 260 has an operation unit main body 261 and a band attachment part 264.

The operation unit main body 261 is formed in a cylindrical shape and has a distal end opening 262 and a proximal end opening 263. A proximal end of the resin sheath 290 is fixed to the distal end opening 262. The wire sheath 280 extends from the proximal end opening 263. The operator can move the wire sheath 280 forward and backward with respect to the resin sheath 290 by moving the wire sheath 280 forward and backward with respect to the operation unit main body 261.

The band attachment part 264 is a member attached to the operation unit main body 261 and has a band insertion hole 265. When a band (not illustrated) that has been passed through the band insertion hole 265 is attached to the endoscope 200, the operation unit main body 261 can be easily fixed to the endoscope 200. When the operation unit main body 261 is fixed to the endoscope 200, the operator can move the wire sheath 280 forward and backward with respect to the resin sheath 290 without holding the operation unit main body 261 by hand.

A rubber plug 266 that comes into contact with the wire sheath 280 is provided at the proximal end opening 263 through which the wire sheath 280 is discharged. A frictional force generated between the wire sheath 280 and the rubber plug 266 can suppress an unintended forward/backward motion of the wire sheath 280 during treatment.

[Basic Configuration of Medical Stapler 100]

Figure 3:
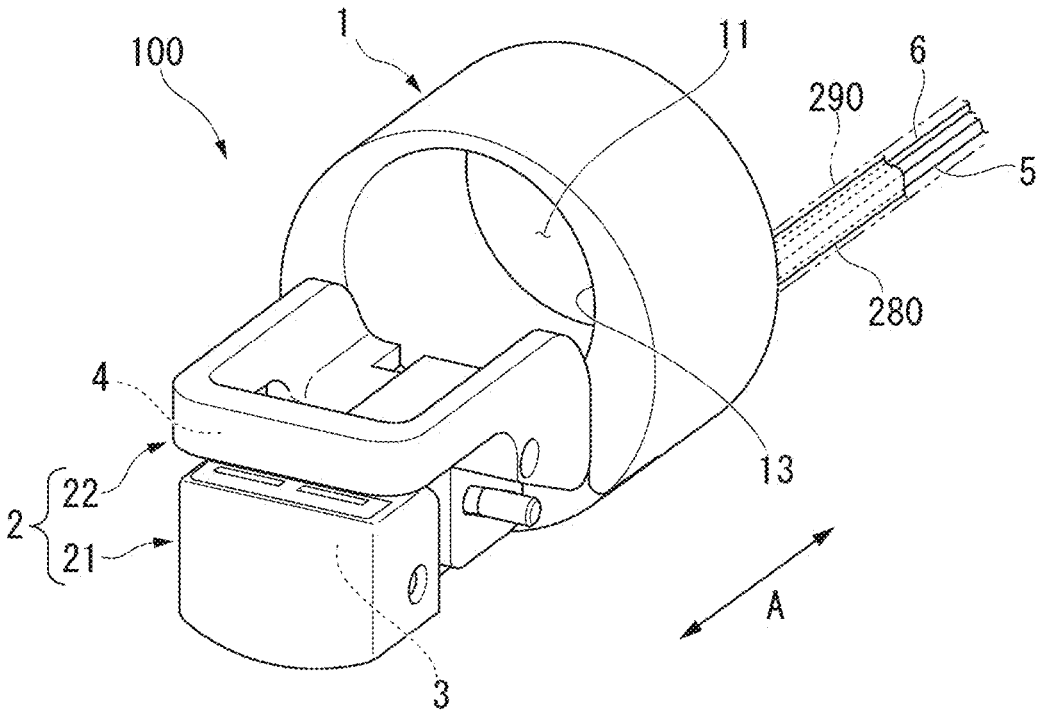
FIG. 3 is a perspective view of a medical stapler 100.

FIG. 3 is a perspective view of the medical stapler 100.

Here, a basic configuration of the medical stapler 100 according to the present invention will be described.

The basic configuration of the medical stapler 100 includes the cap 1, a gripping part (suture assembly) 2, a staple ejection part 3, a staple receiving part 4, the opening/closing operation wire 5, and the ejection operation wire 6. The medical stapler 100 is detachably attached to the distal end part 211 of the insertion part 210.

Figure 4:
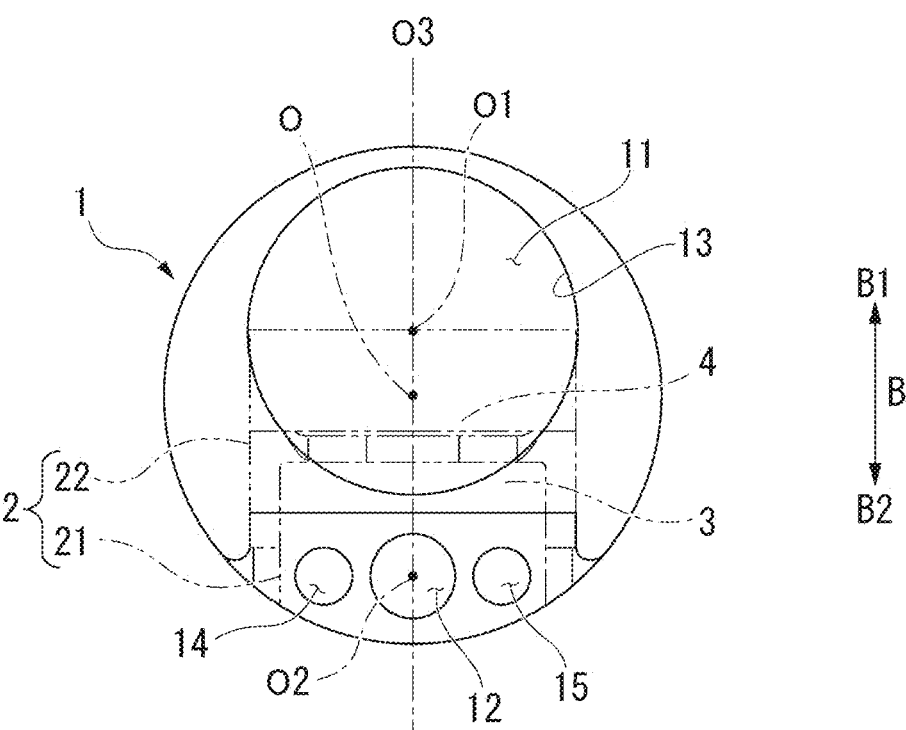
FIG. 4 is a front view of a cap 1.

FIG. 4 is a front view of the cap 1. In FIG. 4, the gripping part 2 is illustrated in a transparent view.

The cap (detachable part) 1 is a member that is detachably attached to the distal end part 211 of the endoscope 200. The cap 1 is formed in a substantially columnar shape and has a first through hole 11 that penetrates in an axial direction A, a second through hole 12 that penetrates in the axial direction A, a third through hole 14 that penetrates in the axial direction A, and a fourth through hole 15 that penetrates in the axial direction A.

The first through hole 11 is a hole into which the distal end part 211 of the insertion part 210 is inserted. A shape of the first through hole 11 is formed to follow an outer shape of the distal end part 211 of the insertion part 210. Therefore, when the distal end part 211 of the endoscope 200 is inserted into the first through hole 11, the cap 1 can be attached to the distal end part 211 of the endoscope 200.

As illustrated in FIG. 4, a central axis O1 of the first through hole 11 in the axial direction A is eccentric with respect to a central axis O of the cap 1 in the axial direction A. A direction in which the central axis O1 is eccentric with respect to the central axis O is defined as an "upward direction B1".

The second through hole 12 is a hole into which the resin sheath 290 is inserted. An inner diameter of the second through hole 12 is substantially the same as an outer diameter of the resin sheath 290. A distal end part of the resin sheath 290 is inserted through the second through hole 12 to be fixed. The wire sheath 280, the opening/closing operation wire 5, and the ejection operation wire 6, which are inserted through the resin sheath 290, are inserted through the second through hole 12 and extend to the distal end side.

As illustrated in FIG. 4, a central axis O2 of the second through hole 12 in the axial direction A is eccentric with respect to the central axis O of the cap 1 in the axial direction A. A direction in which the central axis O2 is eccentric with respect to the central axis O is opposite to the direction (the upward direction B1) in which the central axis O1 is eccentric with respect to the central axis O. A direction in which the central axis O2 is eccentric with respect to the central axis O is defined as a "downward direction B2". In the present embodiment, the upward direction B1 and the downward direction B2 are directions extending in a vertical direction B.

The third through hole 14 and the fourth through hole 15 are formed on both sides of the second through hole 12, with the second through hole 12 interposed therebetween, in a front view from a direction in the axial direction A.

Figure 5:
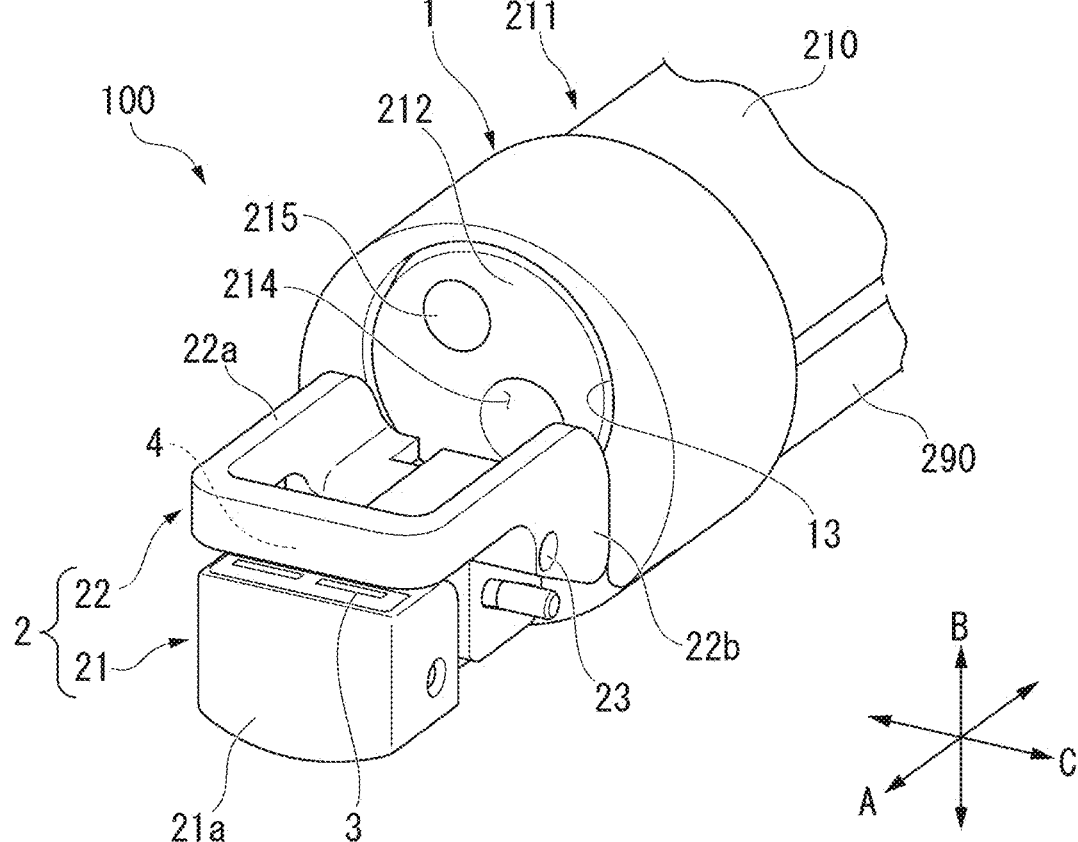
FIG. 5 is a perspective view of the medical stapler 100 with the gripping part 2 in a closed state.
Figure 6:
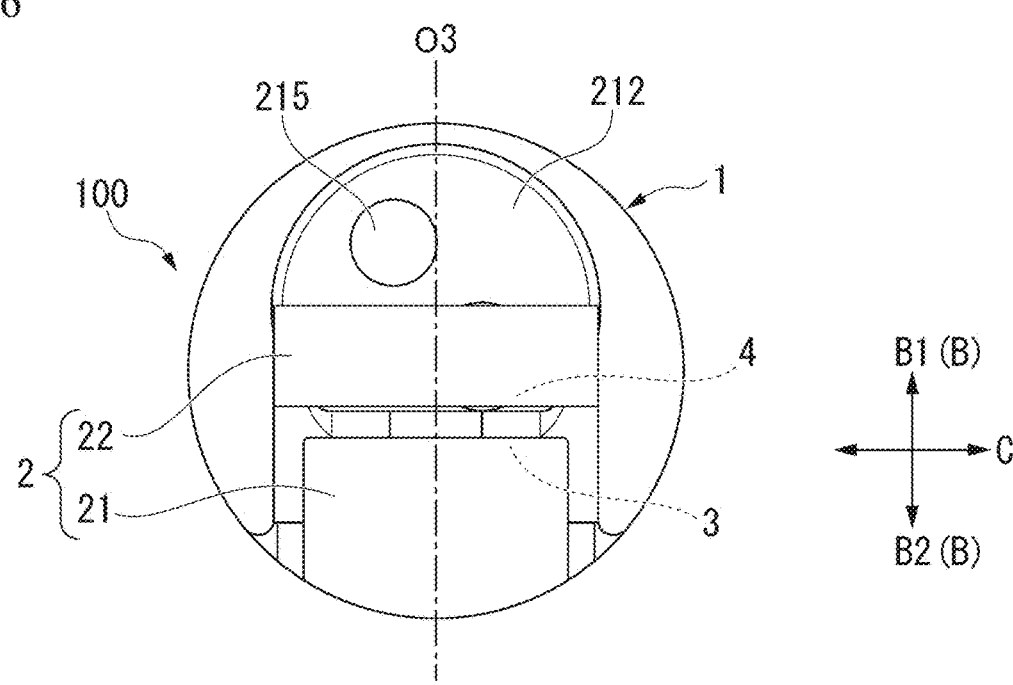
FIG. 6 is a front view of the medical stapler 100 with the gripping part 2 in a closed state.

FIGS. 5 and 6 are a perspective view and a front view of the medical stapler 100 with the gripping part 2 in a closed state.

When the cap 1 is attached to the distal end part 211 of the endoscope 200, as illustrated in FIGS. 5 and 6, the objective lens 215 and the forceps port 214 are exposed from an opening 13 on a distal end side of the first through hole 11 of the cap 1. The operator can observe a treatment target through the objective lens 215 even when the medical stapler 100 is attached to the distal end part 211 of the endoscope 200.

Figure 7:
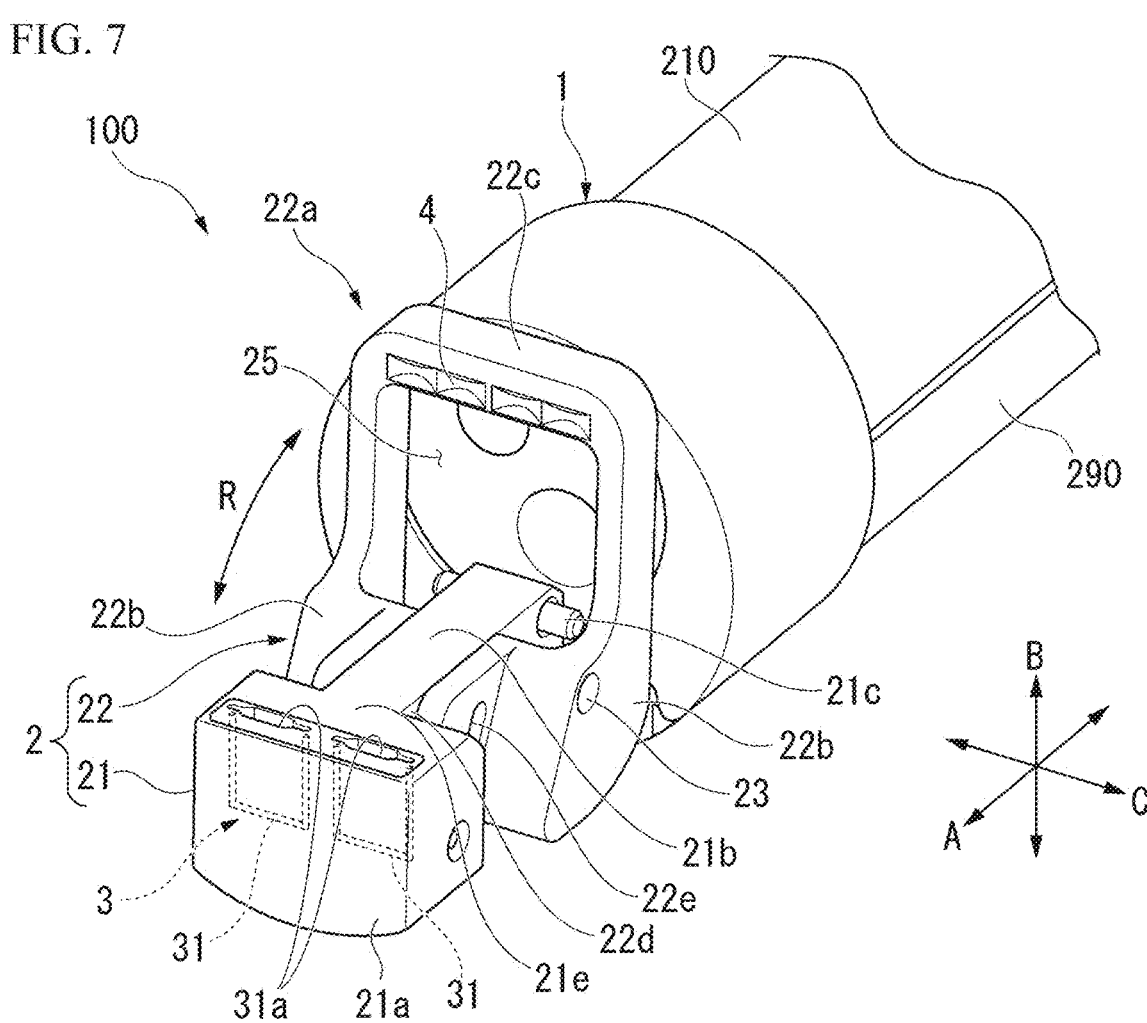
FIG. 7 is a perspective view of the medical stapler 100 with the gripping part 2 in an open state.
Figures 8, 9:
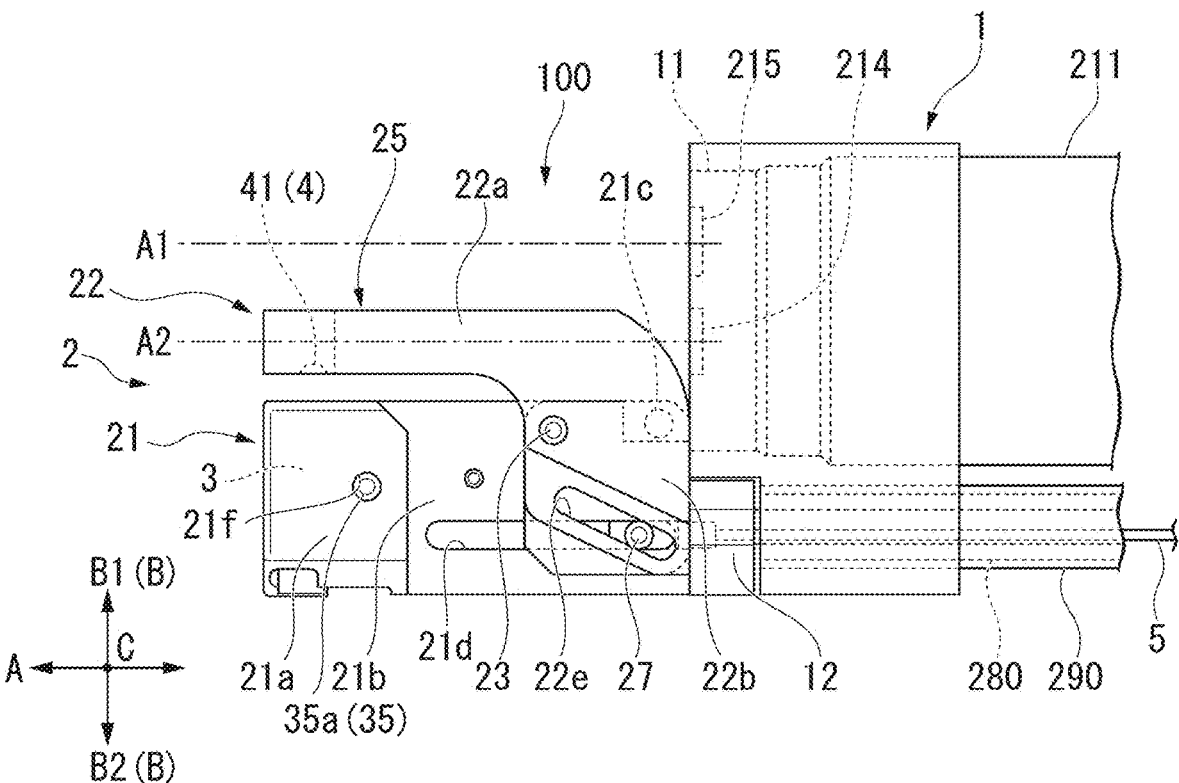
FIG. 8 is a front view of the medical stapler 100 with the gripping part 2 in an open state.
FIG. 9 is a view illustrating the gripping part 2 in a closed state.
Figures 10, 11:
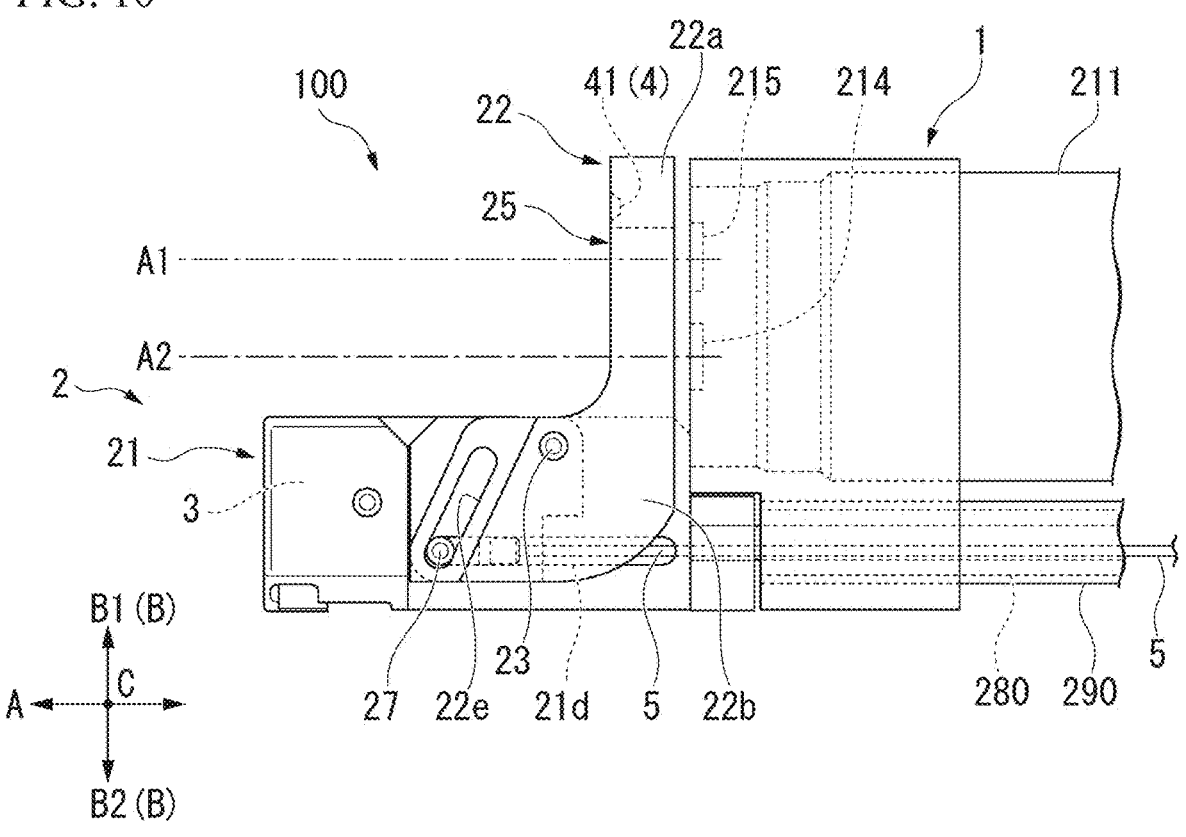
FIG. 10 is a view illustrating the gripping part 2 in an open state.
FIG. 11 is a perspective view illustrating a connection between the first gripping member 21 and the cap 1.

FIGS. 7 and 8 are a perspective view and a front view of the medical stapler 100 with the gripping part 2 in an open state. Further, FIG. 9 is a side view of the medical stapler 100 with the gripping part 2 in a closed state. FIG. 10 is a side view of the medical stapler 100 with the gripping part 2 in an open state.

The gripping part 2 is provided on a distal end side of the cap 1 and is capable of suturing a gripped target tissue with the staple S. The gripping part 2 has a first gripping member 21, a second gripping member 22, an opening/closing rotation shaft 23, and a movable pin 27. The first gripping member 21 and the second gripping member 22 are connected to be openable and closable by the opening/closing rotation shaft 23. The first gripping member 21 and the second gripping member 22 rotate relatively to grip the target tissue. The opening/closing rotation shaft 23 is provided on a distal end side of the cap 1. An axial direction of the opening/closing rotation shaft 23 (the width direction C) is perpendicular to the axial direction A and the vertical direction B of the cap 1. As illustrated in FIG. 8, the gripping part 2 is symmetrically formed with respect to a central axis O3 in the vertical direction B.

FIG. 11 is a perspective view illustrating a connection between the first gripping member 21 and the cap 1.

The first gripping member 21 is connected to the distal end side of the cap 1 to be movable forward and backward. The first gripping member 21 is connected to the cap 1 below the central axis O of the cap 1 in the downward direction B2. Two support members 26 extending to the proximal end side in the axial direction A are attached to the first gripping member 21.

The two support members 26 are hard and elongated members, and support the first gripping member 21 to be movable forward and backward with respect to the cap 1. The two support members 26 are inserted into the third through hole 14 and the fourth through hole 15 to be movable forward and backward in the axial direction A, respectively. That is, the two support members 26, the third through hole 14, and the fourth through hole 15 constitute an advance/retract mechanism of the first gripping member 21.

The first gripping member 21 is supported by the two support members 26 aligned in the width direction C, and therefore does not rotate about the axial direction A as a rotation axis. Also, the two support members 26, when drawing in tissue during a drawing in step S16 described later, have effects of suppressing deflection of the wire sheath 280 and supporting the first gripping member 21 of the gripping part 2 so that it does not deviate from the central axis O2. Further, if a rigidity or the like of the support member 26 is sufficient, the support members 26 may be a single member.

As illustrated in FIG. 11, a distal end part of the wire sheath 280 through which the opening/closing operation wire 5 and the ejection operation wire 6 are inserted is fixed to the first gripping member 21. When the wire sheath 280 moves forward and backward with respect to the resin sheath 290, the first gripping member 21 connected to the wire sheath 280 moves forward and backward with respect to the cap 1.

As illustrated in FIG. 4, the first gripping member 21 is disposed at a position overlapping the second through hole 12 in a front view. On the other hand, as illustrated in FIG.

8, the first gripping member 21 is disposed at a position not overlapping the objective lens 215 and the forceps port 214 of the endoscope 200 in a front view.

As illustrated in FIG. 7, the first gripping member 21 includes a first distal end part 21a and a first main body part 21b, and is formed in a substantially T shape in a plan view. The first distal end part 21a is disposed on a distal end side with respect to the first main body part 21b.

The first distal end part 21a is formed in a substantially rectangular parallelepiped shape. The first distal end part 21a is formed in a rectangular shape extending in an axial direction C of the opening/closing rotation shaft 23 in a plan view. The staple ejection part 3 is provided at the first distal end part 21a. An opening 31a of the staple ejection part 3 is provided on a surface (upper surface 21e) of the first distal end part 21a in the upward direction B1.

The first main body part 21b is an elongated member extending in the axial direction A. A distal end of the first main body part 21b is fixed to the first distal end part 21a. A proximal end of the first main body part 21b is fixed to the cap 1. The first main body part 21b has a contact pin 21c and a first engagement groove 21d.

The contact pin 21c is provided at a proximal end of the first main body part 21b, and comes into contact with the second gripping member 22 in a closed state to restrict a movable range of the second gripping member 22.

As illustrated in FIG. 9, the first engagement groove 21d is a groove penetrating the first main body part 21b in the axial direction C of the opening/closing rotation shaft 23. The first engagement groove 21d extends in the axial direction A.

The second gripping member 22 is attached to the first gripping member 21 to be rotatable by the opening/closing rotation shaft 23. The second gripping member 22 includes a U-shaped member 22a formed in a substantially U shape, and a second main body part 22b supporting the U-shaped member 22a to be rotatable.

The U-shaped member 22a is formed in a substantially U-shape, with both end portions connected to the second main body part 22b and a central portion disposed on the distal end side. The central portion has a second distal end part 22c. The second distal end part 22c is formed in a substantially rectangular parallelepiped shape. The staple receiving part 4 is provided in the second distal end part 22c.

The second main body part 22b is attached to the first main body part 21b of the first gripping member 21 to be rotatable by the opening/closing rotation shaft 23. A guide groove 22d into which the first main body part 21b is inserted is formed in the second main body part 22b. A second engagement groove 22e is formed on both side portions of the guide groove 22d of the second main body part 22b.

The second engagement groove 22e is a groove formed in the second main body part 22b. The second engagement groove 22e is a groove penetrating in the axial direction C. The second engagement groove 22e is formed on a side opposite to the staple receiving part 4 with the opening/closing rotation shaft 23 interposed therebetween in a side view. The second engagement groove 22e is symmetrical with respect to the central axis O3 of the second gripping member 22.

As illustrated in FIG. 7, the second gripping member 22 has a visual space 25 that extends in an opening/closing direction R between the staple receiving part 4 on the distal end side and the opening/closing rotation shaft 23 on the proximal end side. In the present embodiment, the visual space 25 is a space surrounded by sides of the U-shaped member 22*a* formed in a substantially U shape.

The movable pin 27 is engaged with the first engagement groove 21*d* and the second engagement groove 22*e*, and moves forward and backward in the axial direction A along the first engagement groove 21*d*. A distal end of the opening/closing operation wire 5 is attached to the movable pin 27. When the opening/closing operation wire 5 moves forward to the distal end side, as illustrated in FIG. 10, the movable pin 27 rotates the second gripping member 22 about the opening/closing rotation shaft 23 to place the gripping part 2 in an open state. When the opening/closing operation wire 5 moves backward to the proximal end side, as illustrated in FIG. 9, the movable pin 27 rotates the second gripping member 22 about the opening/closing rotation shaft 23 to place the gripping part 2 in a closed state. That is, the opening/closing operation wire 5 is a member that transmits power to enable the gripping part 2 to grip the target tissue by rotating the first gripping member 21 and the second gripping member 22 relative to each other.

When the gripping part 2 is in a closed state, the staple ejection part 3 and the staple receiving part 4 face each other as illustrated in FIG. 6. When the gripping part 2 is in the closed state, a slight gap is formed between the staple ejection part 3 and the staple receiving part 4. When the gripping part 2 is in the closed state, as illustrated in FIGS. 5, 6, and 9, an optical axis A1 of the objective lens 215 passes outside the first gripping member 21 and the second gripping member 22. Also, when the gripping part 2 is in the closed state, a central axis A2 of the forceps port 214 is at a position not overlapping the first gripping member 21 in a front view, but overlapping the second gripping member 22.

When the gripping part 2 is in an open state, the staple receiving part 4 is disposed on the proximal end side with respect to the opening/closing rotation shaft 23 as illustrated in FIG. 10. When the gripping part 2 is in the open state, as illustrated in FIGS. 7, 8, and 10, the staple ejection part 3 and the staple receiving part 4 are disposed on both sides with the optical axis A1 of the objective lens 215 therebetween. When the gripping part 2 is in the open state, the optical axis A1 of the objective lens 215 passes through the visual space 25. Also, when the gripping part 2 is in the open state, the central axis A2 of the forceps port 214 passes through the visual space 25.

Figures 12, 13:
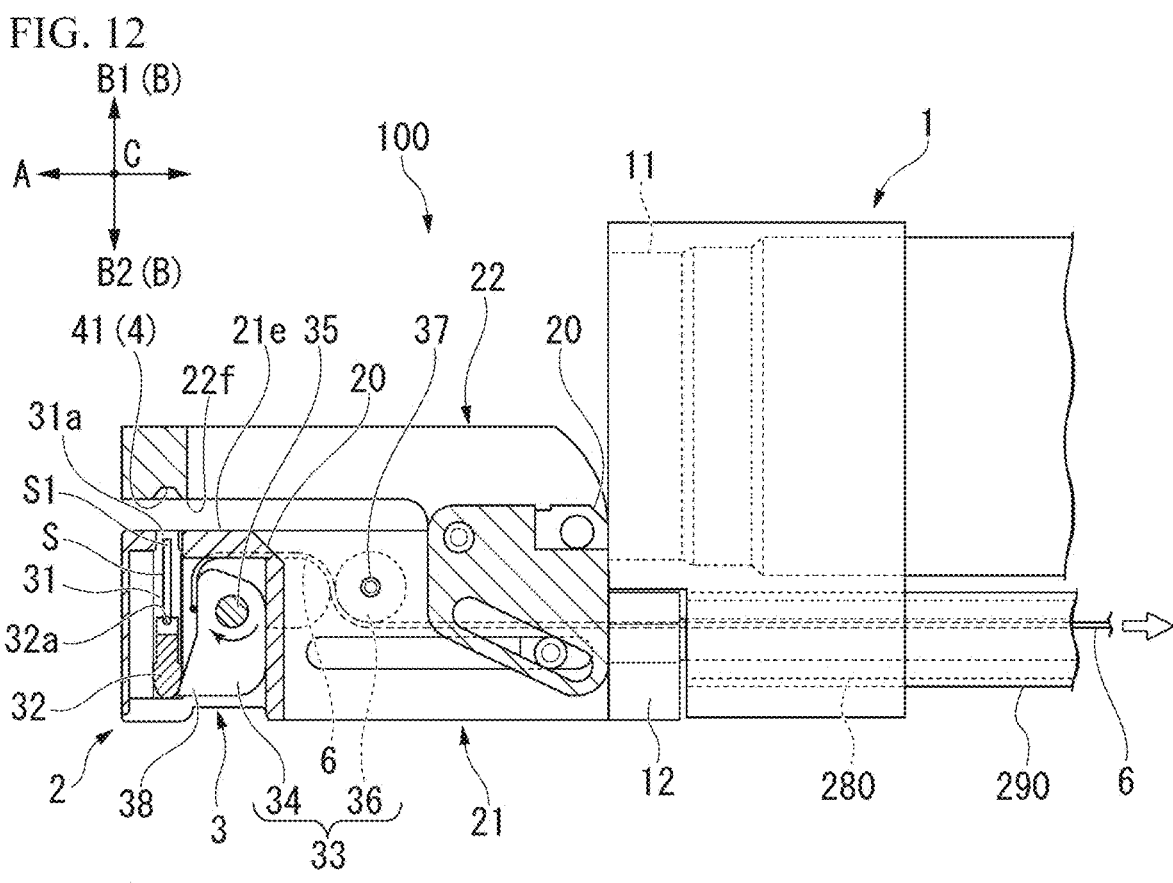
FIG. 12 is a cross-sectional view of the gripping part 2 including a staple ejection part 3.
FIG. 13 is a cross-sectional view of the gripping part 2 after an ejection operation wire 6 has been pulled.

FIG. 12 is a cross-sectional view of the gripping part 2 including the staple ejection part 3.

The staple ejection part 3 is provided at the first distal end part 21*a* of the first gripping member 21, and can store and eject the staple S. The staple ejection part 3 includes a staple storage part 31, a linear moving member (support member) 32, and a rotation member (extrusion member) 33.

The staple storage part 31 is a space for storing the staple S provided at the first distal end part 21*a* of the first gripping member 21. As illustrated in FIG. 7, the first gripping member 21 includes two staple storage parts 31 formed to be aligned in the axial direction C, and can store two U-shaped staples S.

The staple storage part 31 opens in the vertical direction B at the opening 31*a* provided on an upper surface 21*e* of the first distal end part 21*a*. The staple S is stored in the staple storage part 31 through the opening 31*a*. The staple S is stored in the staple storage part 31 with a needle tip S1 of the staple S facing the upward direction B1.

The staple storage part 31 is formed in a substantially rectangular shape with a short side extending in the axial direction A and a long side extending in the axial direction C in a plan view. The staple S stored in the staple storage part 31 has the needle tip S1 at both ends aligned in the axial direction C.

The linear moving member (support member) 32 is a member accommodated in the staple storage part 31 and is movable in the vertical direction B within an internal space of the staple storage part 31. The linear moving member 32 has a recessed part 32*a* that supports the staple S in the upward direction B1. The staple S stored in the staple storage part 31 is fitted into the recessed part 32*a*.

A first pulley (first member) 34 and a second pulley 36 which serve as the rotation member 33 are rotatably attached inside the first gripping member 21, and rotate to move the linear moving member 32 in the vertical direction B. A distal end of the ejection operation wire 6 is connected to the first pulley 34. When the ejection operation wire 6 is pulled, the first pulley 34 can be rotated.

The second pulley 36 is rotatably attached inside the first gripping member 21, and the first pulley 34 is disposed on a distal end side with respect to the second pulley 36. A rotation shaft 35 of the first pulley 34 and a rotation shaft 37 of the second pulley 36 extend in the axial direction C and are substantially parallel to the opening/closing rotation shaft 23 of the gripping part 2. The first pulley 34 has a protruding part (contact part) 38 that supports the linear moving member 32 from a side in the downward direction B2 on a distal end side thereof.

The distal end of the ejection operation wire 6 is connected to the first pulley 34 above the rotation shaft 35 in the upward direction B1. The ejection operation wire 6 extends from the first pulley 34 to the ejection operation unit 270 via the second pulley 36 and passing through the second through hole 12. The reason for providing the second pulley 36 is to adjust a position of the ejection operation wire 6 for smoothly guiding it into the second through hole 12 and to reduce frictional resistance when the ejection operation wire 6 is guided into the second through hole 12. Therefore, the same effect can be obtained even when only the first pulley 34 is used as the rotation member 33, and a component having an R shape with good sliding ability to reduce friction is provided in place of the second pulley 36.

FIG. 13 is a cross-sectional view of the gripping part 2 after the ejection operation wire 6 has been pulled.

When the ejection operation wire 6 is pulled, a side in the upward direction B1 of the first pulley 34 rotates to the proximal end side, and a side in the downward direction B2 of the first pulley 34 rotates to the distal end side. As a result, the protruding part 38 of the first pulley 34 pushes up the linear moving member 32 in the upward direction B1, and the stored staple S is ejected in the upward direction B1 from the opening 31*a*. That is, the ejection operation wire 6 is a member that transmits power to enable the gripping part 2 to eject the staple S.

The staple receiving part 4 is provided on a lower surface 22*f* of the second distal end part 22*c* of the second gripping member 22. A plurality of pockets 41 that can receive the staples S ejected from the staple ejection part 3 are provided in the staple receiving part 4. In the present embodiment, two U-shaped staples are ejected from the staple ejection part 3, and therefore four pockets are provided in the staple receiving part 4. When the gripping part 2 is in a closed state, the opening 31*a* through which the staple S is ejected and the pocket 41 of the staple ejection part 3 face each other as illustrated in FIG. 12.

Figure 14:
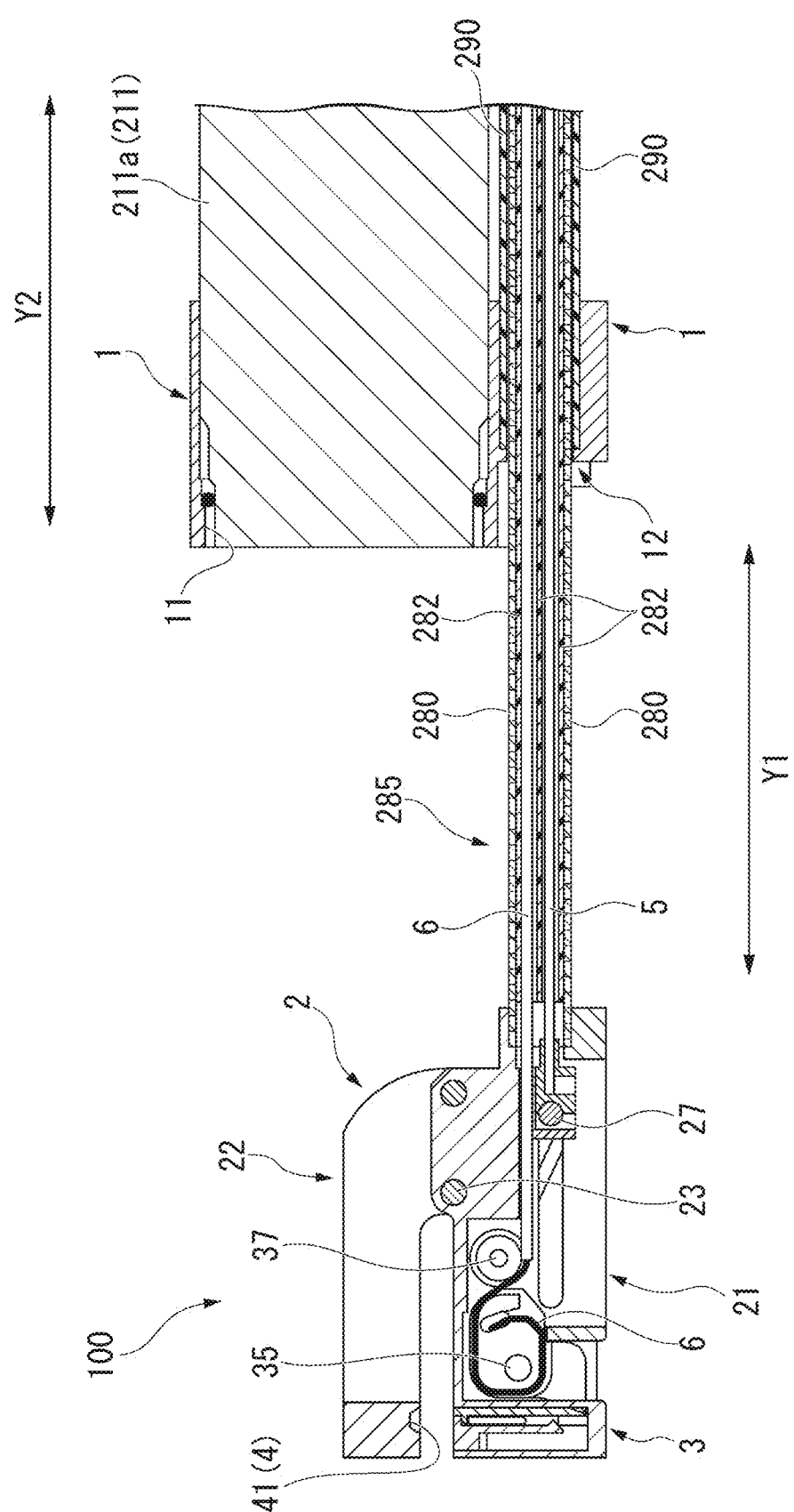
FIG. 14 is a cross-sectional view of the gripping part 2 that has moved forward and the cap 1.

FIG. 14 is a cross-sectional view of the gripping part 2 that has moved forward and the cap 1. FIG. 14 illustrates a configuration of one embodiment (first embodiment to be described later) of the medical stapler 100 according to the present invention.

Even when the gripping part 2 has moved forward, it is connected to the opening/closing operation wire 5 and the ejection operation wire 6 which are inserted through the wire sheath 280. The operator can move the opening/closing operation wire 5 and the ejection operation wire 6 forward and backward even when the gripping part 2 has moved forward.

The gripping part 2 illustrated in FIG. 14 is disposed at the most forward position with respect to the cap 1. A length Y1 of a distal end part 285 of the wire sheath 280 that can protrude from the second through hole 12 of the cap 1 to the distal end side is equal to or less than a length Y2 of the hard portion 211a at the distal end part 211 of the endoscope 200.

[Basic Operation of Medical Stapler 100]

Figure 15:
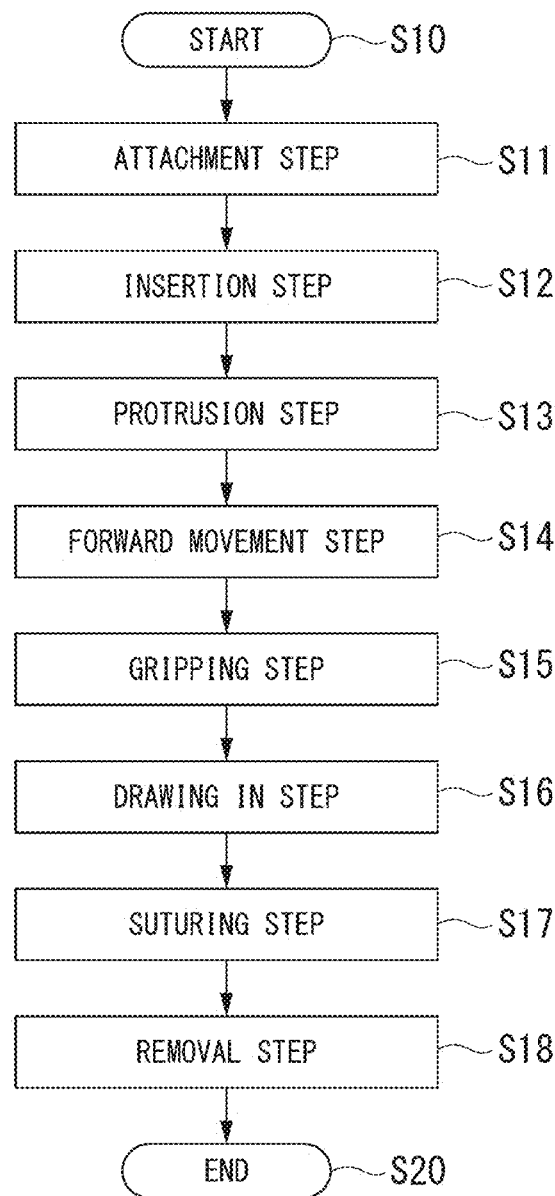
FIG. 15 is a flowchart showing a manipulation procedure performed by an operator using the medical stapler 100.
Figure 16:
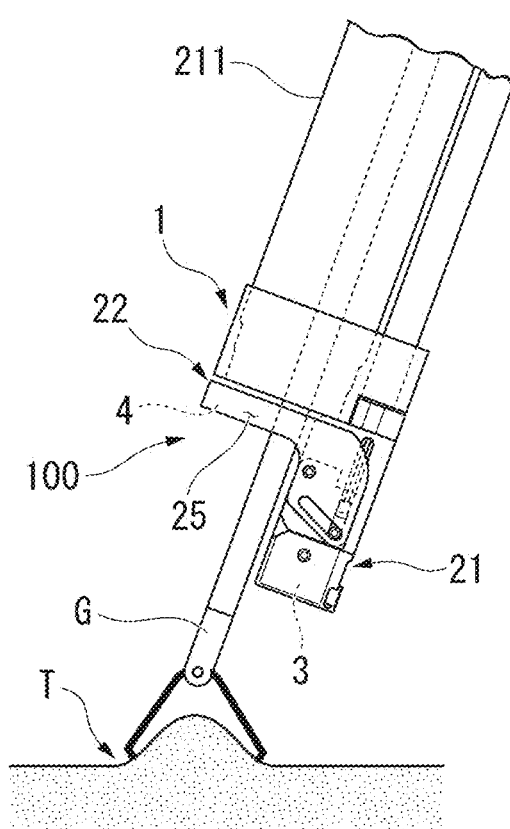
FIG. 16 is a view illustrating an operation of a gripping step S15 by the medical stapler 100.

Next, a basic operation of the medical stapler 100 according to the present invention will be described. FIG. 15 is a flowchart showing a manipulation procedure performed by the operator using the medical stapler 100. FIGS. 16 to 19 are views illustrating an operation of the medical stapler 100 according to the present invention.

The operator attaches the medical stapler 100 to the distal end part 211 of the endoscope 200 (attachment step S11). The operator inserts the medical stapler 100 and the endoscope 200 into the body (insertion step S12).

The operator brings the distal end part 211 of the endoscope 200, to which the medical stapler 100 is attached, closer to a treatment target T (an example of target tissue). The operator operates the opening/closing operation part 250 to move the opening/closing operation wire 5 forward, thereby placing the gripping part 2 in an open state. Since the optical axis A1 of the objective lens 215 passes through the visual space 25, the operator can observe the treatment target T through the imaging unit of the endoscope 200. Also, since the central axis A2 of the forceps port 214 passes through the visual space 25, as illustrated in FIG. 10, the operator can treat the treatment target T by causing gripping forceps (treatment tool) G to protrude from the forceps port 214 (protrusion step S13).

Figure 17:
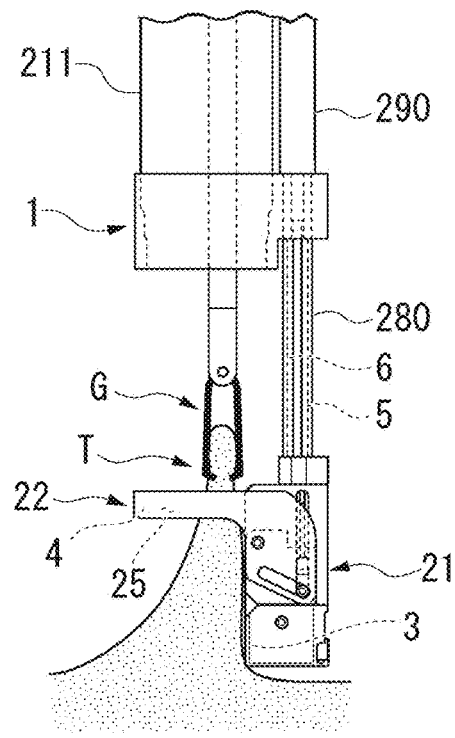
FIG. 17 is a view illustrating an operation of a drawing in step S16 by the medical stapler 100.

If the treatment target T is positioned at a place to which it is difficult for the endoscope 200 to approach, as illustrated in FIG. 17, the operator moves the wire sheath 280 to move forward to move the gripping part 2 forward (forward movement step S14). The operator causes the gripping forceps G to protrude from the visual space (pass-through space) 25 of the gripping part 2 that has moved forward to grip the treatment target T (gripping step S15).

As illustrated in FIG. 17, the operator moves the gripping forceps G backward with the treatment target T gripped by the gripping forceps G. The operator moves the gripping forceps G backward until a distal end of the gripping forceps G passes through the visual space (pass-through space) 25, thereby drawing in the treatment target T until the treatment target T passes through the visual space (pass-through space) 25. As a result, the treatment target T is disposed on the proximal end side with respect to the staple ejection part 3. The operator may move the gripping part 2 forward with respect to the gripping forceps G to draw in the treatment target T. That is, the gripping forceps G is moved backward relative to the gripping part 2 to draw in the treatment target T (drawing in step S16).

As illustrated in FIG. 17, since the first gripping member 21 presses down a peripheral portion of the treatment target T, it is easier for the operator to draw in the treatment target T with the gripping forceps G.

The forward movement step S14 may be implemented before the gripping step S15 or before the drawing in step S16. In either case, the first gripping member 21 can press down the peripheral portion of the treatment target T in the drawing in step S16.

Figure 18:
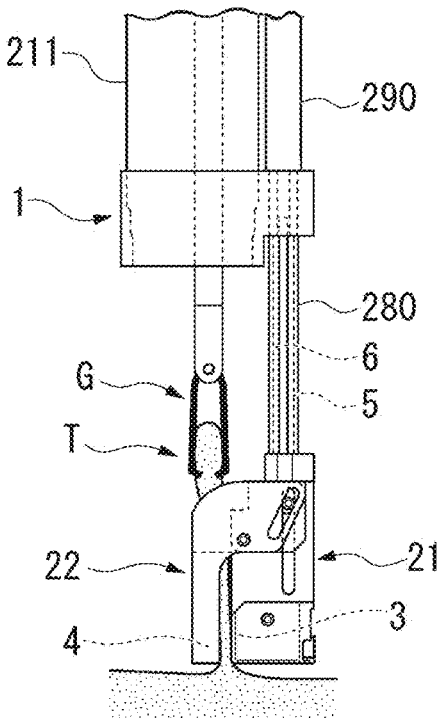
FIG. 18 is a view illustrating an operation of a suturing step S17 by the medical stapler 100.

As illustrated in FIG. 18, the operator operates the opening/closing operation part 250 to move the opening/closing operation wire 5 backward, thereby placing the gripping part 2 in a closed state. The treatment target T is sandwiched between the staple ejection part 3 of the first gripping member 21 and the staple receiving part 4 of the second gripping member 22.

When the gripping part 2 is in a closed state, since a part of the treatment target T gripped by the gripping forceps G can be accommodated in the space (visual space 25) formed by the U-shaped member 22a and the second main body part 22b of the second gripping member 22, there is an effect that the treatment target T sandwiched between the staple ejection part 3 and the staple receiving part 4 is less likely to escape.

When the gripping part 2 is in a closed state, as illustrated in FIG. 9, the optical axis A1 of the objective lens 215 passes outside of the first gripping member 21 and the second gripping member 22. Therefore, even when the gripping part 2 is in the closed state, the operator can observe the treatment target T through the imaging unit of the endoscope 200.

With the treatment target T sandwiched between the staple ejection part 3 and the staple receiving part 4 as illustrated in FIG. 18, the operator operates the ejection operation unit 270 to pull the ejection operation wire 6, thereby ejecting the stored staple S toward the staple receiving part 4. The needle tip S1 of the staple S penetrate through the treatment target T and is bent by coming into contact with the pocket 41 of the staple receiving part 4. As a result, the treatment target T is sutured (suturing step S17).

Figure 19:
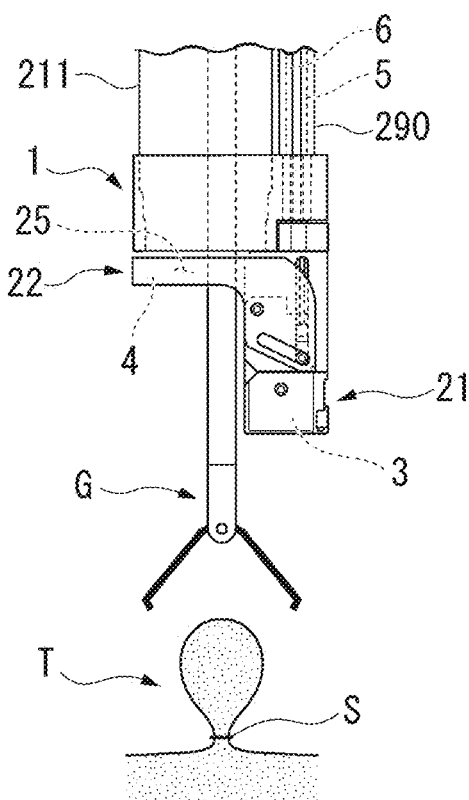
FIG. 19 is a view illustrating an operation of a removal step S18 by the medical stapler 100.

As illustrated in FIG. 19, the operator operates the opening/closing operation unit 250 to bring the gripping part 2 into the open state again. The operator separates the gripping forceps G from the treatment target T and completes the suturing treatment. The operator removes the medical stapler 100 and the endoscope 200 from the body (removal step S18).

Further, in the insertion step S12 and the removal step S18, the operator disposes the gripping part 2 at the most backward position to make it easier for the medical stapler 100 to pass through the body.

<Configuration of Each Embodiment of Medical Stapler 100>

Next, a configuration of each embodiment of the medical stapler used in the above-described medical system 300 according to the present invention will be described in detail.

Medical Stapler 100A of First Embodiment

First, a medical stapler 100A of a first embodiment will be described.

The medical stapler 100A of the present embodiment is configured to directly restrict movement of a staple S.

Figure 20:
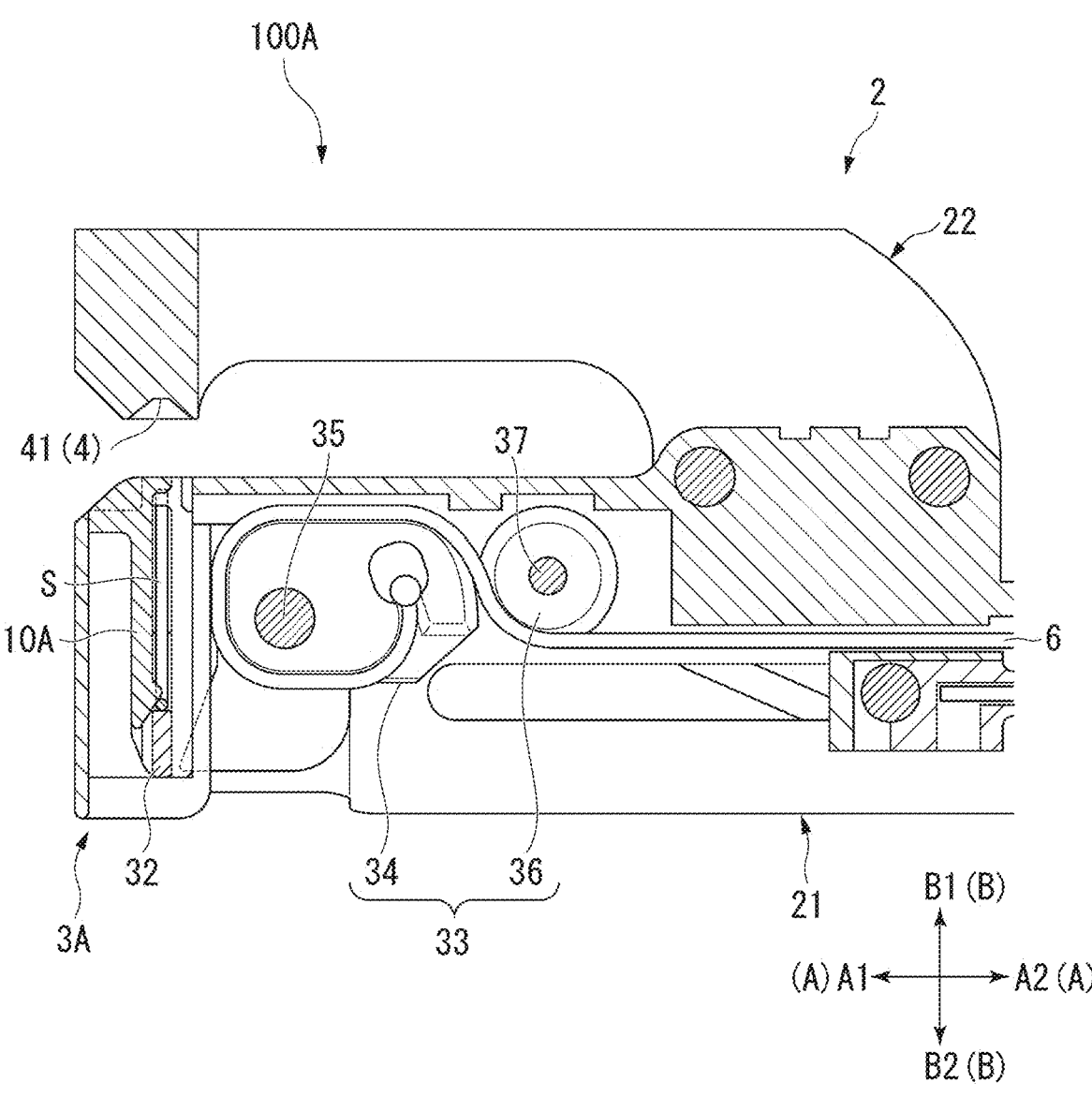
FIG. 20 is a cross-sectional view illustrating a configuration of a medical stapler 100A of a first embodiment.

FIG. 20 is a cross-sectional view illustrating a configuration of the medical stapler 100A of the first embodiment.

As illustrated in FIG. 20, the medical stapler 100A of the first embodiment includes a staple ejection part 3A having a snap fit structure (ejection restriction structure) 10A capable of locking onto the staple S. That is, the staple ejection part 3A has the snap fit structure 10A in addition to the staple storage part 31, the linear moving member 32, and the rotation member 33 described above.

The snap fit structure 10A is provided in a first distal end part 21a of a first gripping member 21, and is provided on a distal end side of the staple storage part 31 to be exposed to the staple storage part 31.

The snap fit structure 10A has a locking part 10a protruding toward the staple S stored in the staple storage part 31 on a lower end side (B2 side) thereof. The locking part 10a locks onto a part of the staple S stored in the staple storage part 31 from the upward direction B1 side.

The snap fit structure 10A extends in an ejection direction (vertical direction B) of the staple S stored in the staple storage part 31, and is configured so that the lower end side (B2 side) is displaceable in the axial direction A using the upper end side (B1 side) as a fulcrum. Specifically, the snap fit structure 10A is displaceable between an "initial position (restriction position)" in which the locking part 10a locks onto a part of the staple S from the upward direction B1 to restrict movement of the staple S, and a "release position" in which the locking part 10a is separated from the staple S to allow the staple S to move.

In the snap fit structure 10A, the locking part 10a is at the "initial position" during each step other than the suturing step S17, and movement of the staple S to the upward direction B1 side can be restricted.

Further, a shape of the locking part 10a illustrated in FIG. 20 is just an example and other shapes may be used.

Figure 21A:
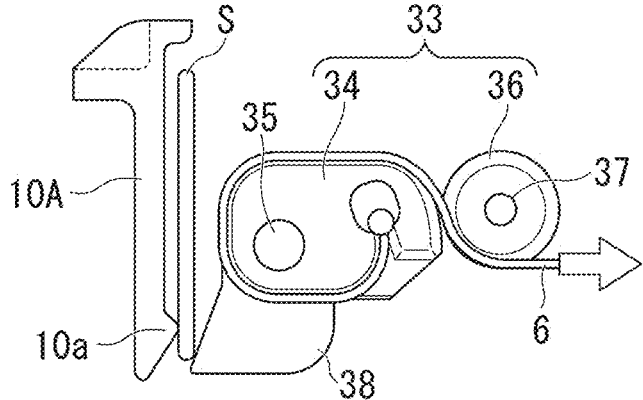
FIG. 21A is a view illustrating an operation of a suturing step of the medical stapler 100A of the first embodiment.
Figure 21B:
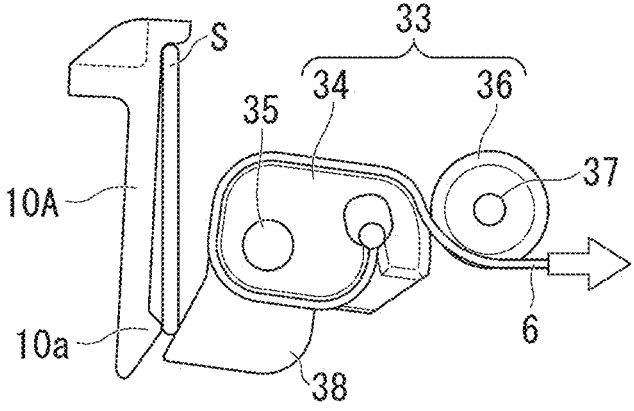
FIG. 21B is a view illustrating an operation of the suturing step following FIG. 21A.
Figure 21C:
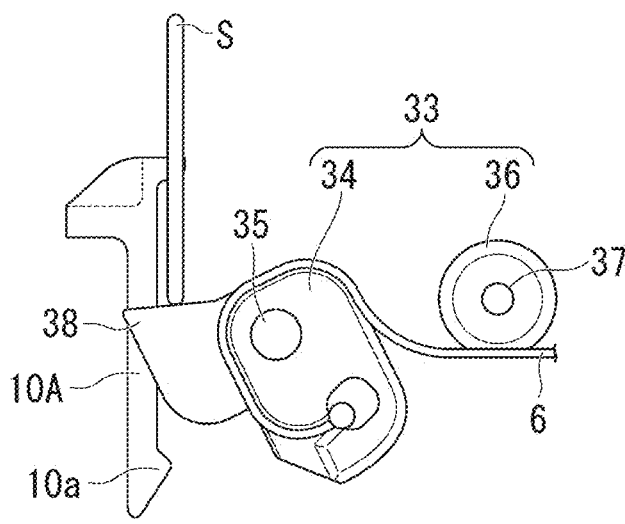
FIG. 21C is a view illustrating an operation of the suturing step following FIG. 21B.

FIG. 21A is a view illustrating an operation of a suturing step of the medical stapler 100A of the first embodiment. FIG. 21B is a view illustrating an operation of the suturing step following FIG. 21A. FIG. 21C is a view illustrating an operation of the suturing step following FIG. 21B.

While the above-described steps S10 to S16 (FIG. 15) are being performed, since the ejection operation wire 6 is not being pulled, the snap fit structure 10A remains locked onto the staple S (FIG. 21A). At this time, a first pulley 34 of the rotation member 33 is separated from the linear moving member 32.

In the suturing step S17, when the wire sheath operation unit 260 is operated and the ejection operation wire 6 is pulled with the treatment target T sandwiched between the staple ejection part 3A and a staple receiving part 4, as illustrated in FIG. 21B, the first pulley 34 of the rotation member 33 rotates around an axis of a rotating shaft 35, thereby pushing up the linear moving member 32 from a side in the downward direction B2. When the linear moving member 32 is pushed up by rotation of the first pulley 34, the staple S rises while pushing aside the snap fit structure 10A that has locked onto the staple S. That is, a lower end side (downward direction B2 side) of the snap fit structure 10A is displaced forward with an upper end side (upward direction B1 side) thereof as a fulcrum, thereby the locking state of the snap fit structure 10A with respect to the staple S is released. At this time, a load associated with the rotation of the first pulley 34 (a pulling force (second tension) applied to the ejection operation wire 6) is larger than a locking force of the snap fit structure 10A with respect to the staple S. Therefore, when the ejection operation wire 6 is pulled in the suturing step S17, the hold on the staple S by the snap fit structure 10A is released, and the staple S is smoothly ejected as illustrated in FIG. 21C.

According to the medical stapler 100A of the present embodiment, even if an unintended first tension (a tension equal to or less than the pulling force applied by the operator) is generated in the ejection operation wire 6 when the endoscope 200 is inserted or removed or in a step other than the suturing step S17, the snap fit structure 10A locks onto the staple S stored in the staple ejection part 3A, thereby restricting movement of the staple S and making it possible to curb unintended falling off of the staple S from the staple storage part 31.

On the other hand, when the ejection operation wire 6 is pulled and the first pulley 34 rotates to apply a force of a certain level or more to the snap fit structure 10A, the restriction on the staple S by the snap fit structure 10A is released and the staple S is smoothly ejected. Since the snap fit structure 10A is provided inside a housing of the staple ejection part 3A, and movement of the ejection operation wire 6 is not hindered, ease of insertion of the endoscope 200 into the lumen is satisfactory.

Therefore, it is possible to obtain the medical stapler 100 that can curb unintended falling off of the staple without decreasing ease of insertion of the endoscope 200 into the lumen.

Modified Example of First Embodiment

A modified example of the medical stapler 100A of the first embodiment will be described.

Figure 22A:
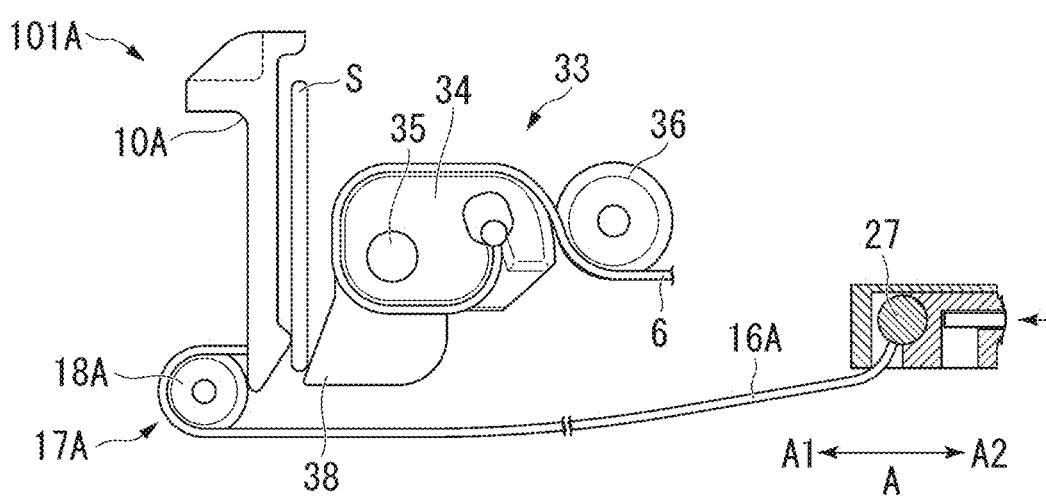
FIG. 22A is a view for explaining a schematic configuration and operation of a modified example of the medical stapler 100A of the first embodiment.
Figure 22B:
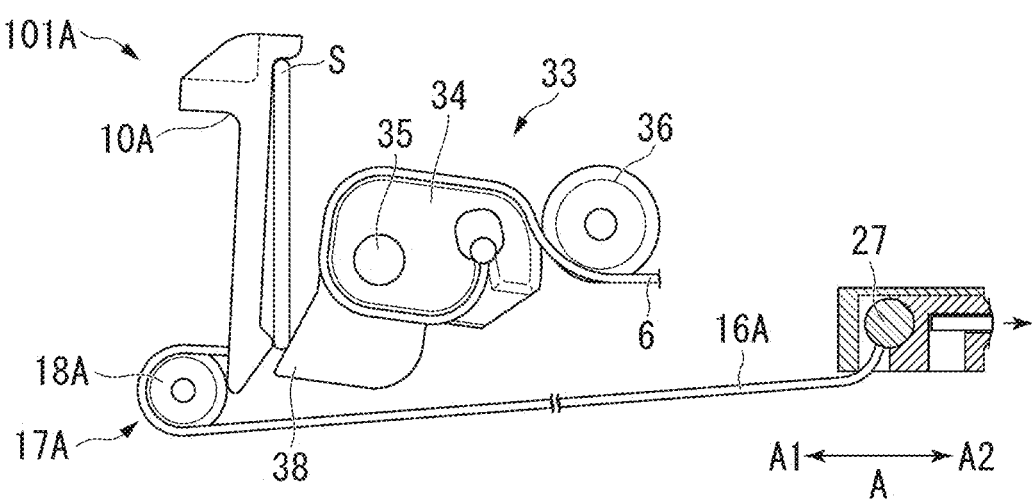
FIG. 22B is a view for explaining a schematic configuration and operation of the modified example of the medical stapler 100A of the first embodiment.

FIGS. 22A and 22B are views for explaining a schematic configuration and operation of a modified example of the medical stapler 100A of the first embodiment.

As illustrated in FIGS. 22A and 22B, a medical stapler 101A of a modified example of the first embodiment has a snap-fit operation part 17A. The snap-fit operation part 17A has a connection wire 16A and a third pulley 18A.

The connection wire 16A extends in the axial direction A, with one end side connected to the snap fit structure 10A, and the other end side connected to the movable pin 27 described above. One end side of the connection wire 16A is connected to a front surface of the snap fit structure 10A. The movable pin 27 is a member that moves forward and backward in the axial direction as the gripping part 2 opens and closes. The third pulley 18A is provided on a distal end side in the axial direction of the snap fit structure 10A. One end side of the connection wire 16A is wound around the third pulley 18A from a forward direction A1 side in the axial direction A by about half a turn, and the one end side of the connection wire 16A is folded back to a rearward side.

In the modified example of the first embodiment, when the gripping part 2 is in an open state as illustrated in FIG. 22A, the movable pin 27 is positioned at a most distal end side of a movable range thereof in the axial direction A, and the connection wire 16A is pushed out to the forward direction A1 side in the axial direction A. Since one end side of the connection wire 16A is folded back to a rear end side (rearward direction A2 side) via the third pulley 18A, the snap fit structure 10A connected to the one end side of the connection wire 16A is pressed toward the rear end side (the rearward direction A2 side) in the axial direction A and locks onto the staple S in the staple storage part 31.

Also, when the gripping part 2 is in a closed state as illustrated in FIG. 22B, the movable pin 27 is positioned at a rearmost end side (rearward direction A2 side) of the movable range in the axial direction A, and the connection wire 16A is pulled to the rear end side (the rearward direction A2 side). The snap fit structure 10A is placed in a state of being pulled to the forward direction A1 side by the connection wire 16A which has been pulled rearward, and the locking part 10a is separated from the staple S. That is, the locking part 10a of the snap fit structure 10A is not locked onto the staple S. In this way, the connection wire 16A moves in the axial direction A as the gripping part 2 opens and closes, and thereby engagement and disengagement of the snap fit structure 10A with the staple S are performed.

According to the modified example of the first embodiment, when the gripping part 2 is brought into an open state in the gripping step S15 described above, since the snap fit structure 10A locks onto the staple S, falling off of the staple S can be suppressed when the treatment target T is gripped by the gripping forceps G.

In the first embodiment and the modified example described above, it has been configured such that the snap fit structure 10A directly presses down the staple S, but the present invention is not limited to the configuration described above as long as it is possible to restrict ejection of the staple S. For example, a configuration in which the snap fit structure 10A locks onto the linear moving member 32 that supports the staple S, instead of the staple S, may be used. When the rise of the linear moving member 32 is suppressed by the snap fit structure 10A, it is possible to restrict ejection of the staple S.

Medical Stapler 100B According to Second Embodiment

Next, a medical stapler 100B of a second embodiment will be described.

The medical stapler 100B in the present embodiment is configured to prevent a staple S from being unintentionally ejected by restricting rotation of a first pulley 34 of a rotation member 33.

Figure 23A:
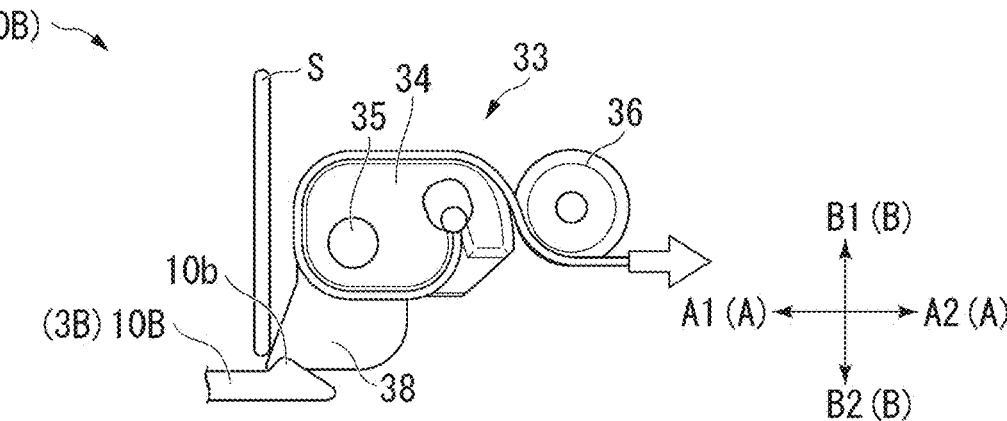
FIG. 23A is a view illustrating an operation of a suturing step of a medical stapler 100B of the second embodiment.
Figure 23B:
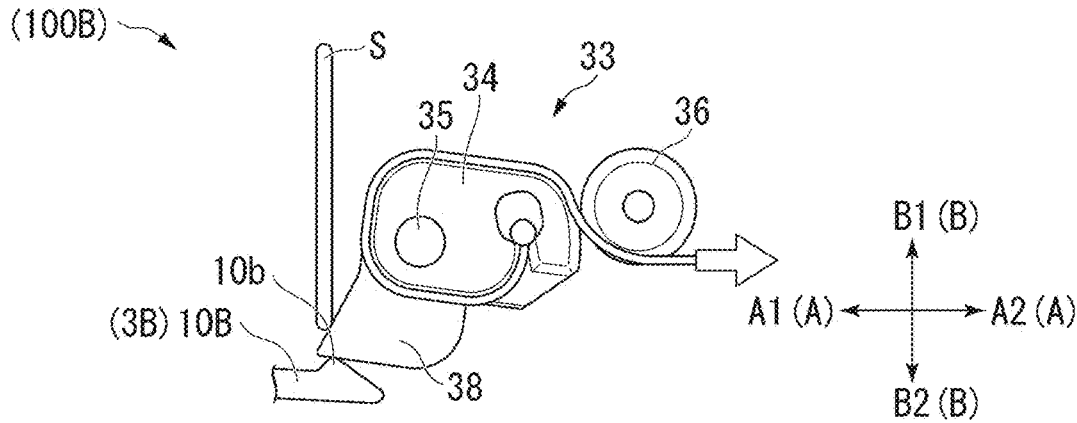
FIG. 23B is a view illustrating an operation of the suturing step following FIG. 23A.
Figure 23C:
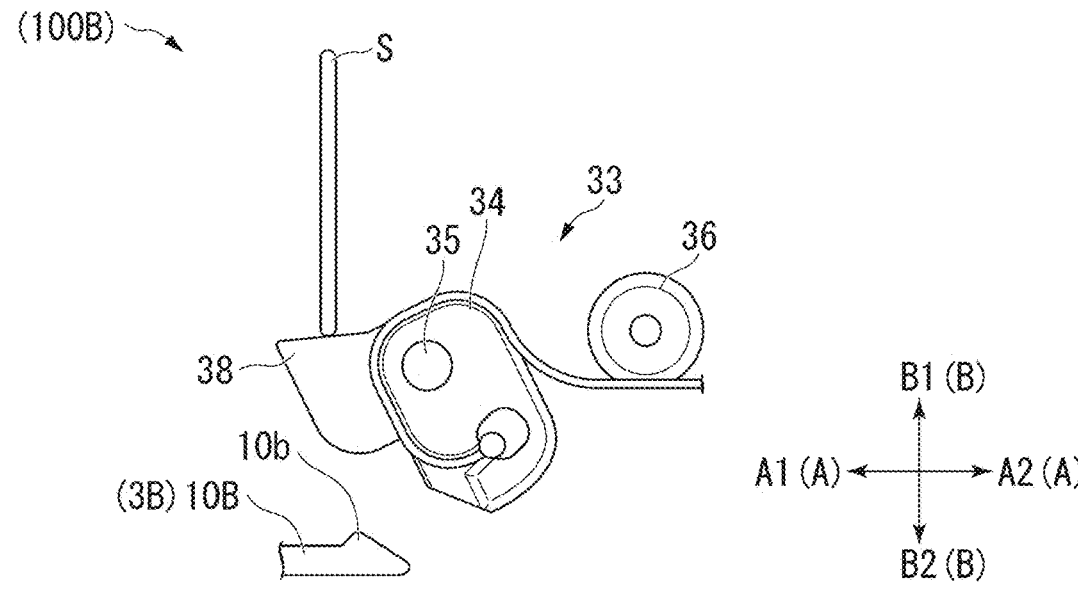
FIG. 23C is a view illustrating an operation of the suturing step following FIG. 23B.

FIGS. 23A, 23B, and 23C are views schematically illustrating a configuration of the medical stapler 100B of the second embodiment.

As illustrated in FIGS. 23A to 23C, the medical stapler 100B of the second embodiment includes a staple ejection part 3B having a snap fit structure (ejection restriction structure) 10B that can be locked onto the rotation member 33. That is, the staple ejection part 3B has the snap fit structure 10B in addition to the staple storage part 31, the linear moving member 32, and the rotation member 33 described above.

The snap fit structure 10B is provided, for example, in the first distal end part 21a of the first gripping member 21 described above, on a side in the downward direction B2 with respect to the staple storage part 31 (see FIG. 20). The snap fit structure 10B extends in the axial direction A, and is configured so that one axial end side (forward direction A1 side) serves as a base point to allow the other axial end side (rearward direction A2 side) to be displaceable in the vertical direction B.

Further, the snap fit structure 10B is not limited to this configuration, and may be configured such that one axial end side (forward direction A1 side) is displaceable in the vertical direction B with the other axial end side (the rearward direction A2 side) as a base point.

The snap fit structure 10B is disposed on the forward direction A1 side with respect to the first pulley 34 of the rotation member 33 in the axial direction A and on a front side of the first pulley 34 in a rotation direction. The snap fit structure 10B has a locking part 10b that can be locked onto the first pulley 34 on the rearward direction A2 side in the axial direction A. The locking part 10b faces a distal end surface of the first pulley 34 and locks onto the first pulley 34 from the forward direction A1 side in the axial direction A. Thereby, rotation of the first pulley 34 around an axis of a rotation shaft 35 can be restricted in each step other than the suturing step S17.

Further, a shape of the locking part 10b illustrated in FIGS. 23A to 23C is merely an example and other shapes may be used.

FIG. 23A is a view illustrating an operation of a suturing step of the medical stapler 100B of the second embodiment. FIG. 23B is a view illustrating an operation of the suturing step following FIG. 23A. FIG. 23C is a view illustrating an operation of the suturing step following FIG. 23B.

While the above-described steps S10 to S16 (FIG. 15) are being performed, since the ejection operation wire 6 is not being pulled, the snap fit structure 10B remains locked onto the first pulley 34 of the rotation member 33 (FIG. 23A).

In the suturing step S17, when the wire sheath operation unit 260 is operated and the ejection operation wire 6 is pulled with the treatment target T sandwiched between the staple ejection part 3B and the staple receiving part 4, as illustrated in FIG. 23B, the first pulley 34 of the rotation member 33 rotates around an axis of the rotating shaft 35, and a rear end side (the rearward direction A2 side) of the snap fit structure 10B in the axial direction A is displaced in the downward direction B2 with the front end side (the forward direction A1 side) thereof as a fulcrum. Thereby, the snap fit structure 10B is released from the locked state with the first pulley 34. As illustrated in FIG. 23C, when the first pulley 34 further rotates around the axis of the rotation shaft 35, the linear moving member 32 is pushed up from a side in the downward direction B2, and the staple S is released. At this time, a load associated with the rotation of the first pulley 34 (a pulling force of the ejection operation wire 6) is larger than a locking force of the snap fit structure 10B with respect to the first pulley 34. Therefore, when the ejection operation wire 6 is pulled, the hold on the first pulley 34 is released by the snap fit structure 10B, and the staple S is smoothly ejected.

According to the medical stapler 100B of the present embodiment, even if an unintended first tension (a tension equal to or less than the pulling force applied by the operator) is generated in the ejection operation wire 6 when the endoscope 200 is inserted or removed or in a step other than the suturing step S17, since rotation of the first pulley 34 is restricted when the snap fit structure 10B locks onto the first pulley 34 before it rotates, the staple S being pushed out of the staple storage part 31 due to unintended rotation of the first pulley 34 can be suppressed.

On the other hand, when the ejection operation wire 6 is pulled and the first pulley 34 rotates to apply a force of a certain level or more to the snap fit structure 10B, the restriction on the first pulley 34 by the snap fit structure 10B is released, the first pulley 34 rotates further, the linear moving member 32 is pushed up, and the staple S is ejected from the staple storage part 31.

Modified Example of Second Embodiment

A modified example of the medical stapler 100B of the second embodiment will be described. In the following description, a detailed description of the same operation and configuration as the modified example of the medical stapler 100A of the first embodiment described above will be omitted, and description will be made focusing on different points.

Figure 24A:
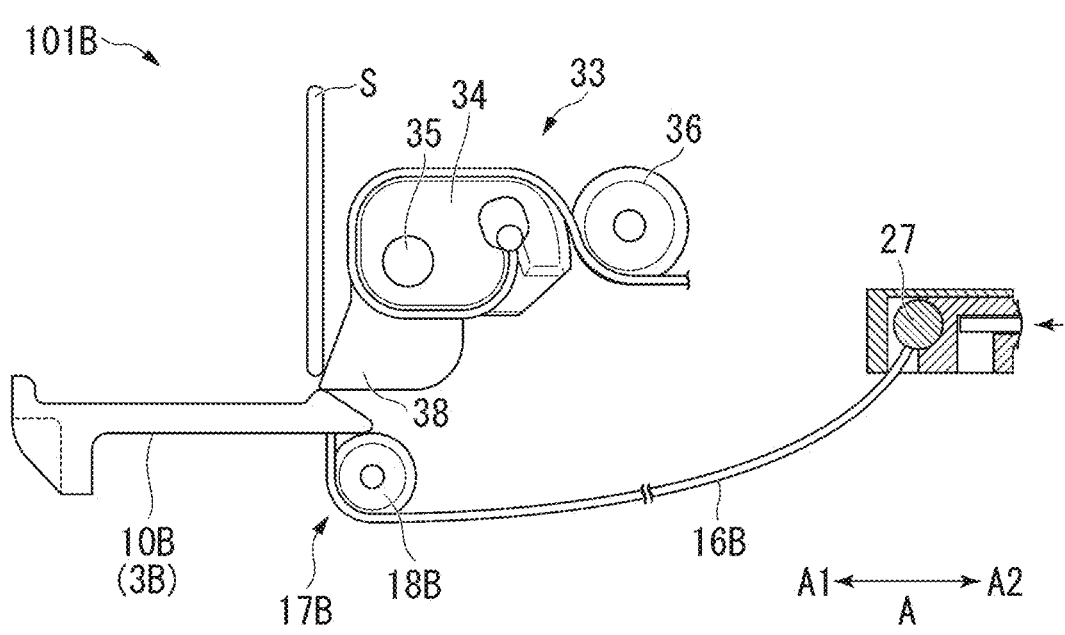
FIG. 24A is a view for explaining a schematic configuration and operation of a modified example of the medical stapler 100B of the second embodiment.
Figure 24B:
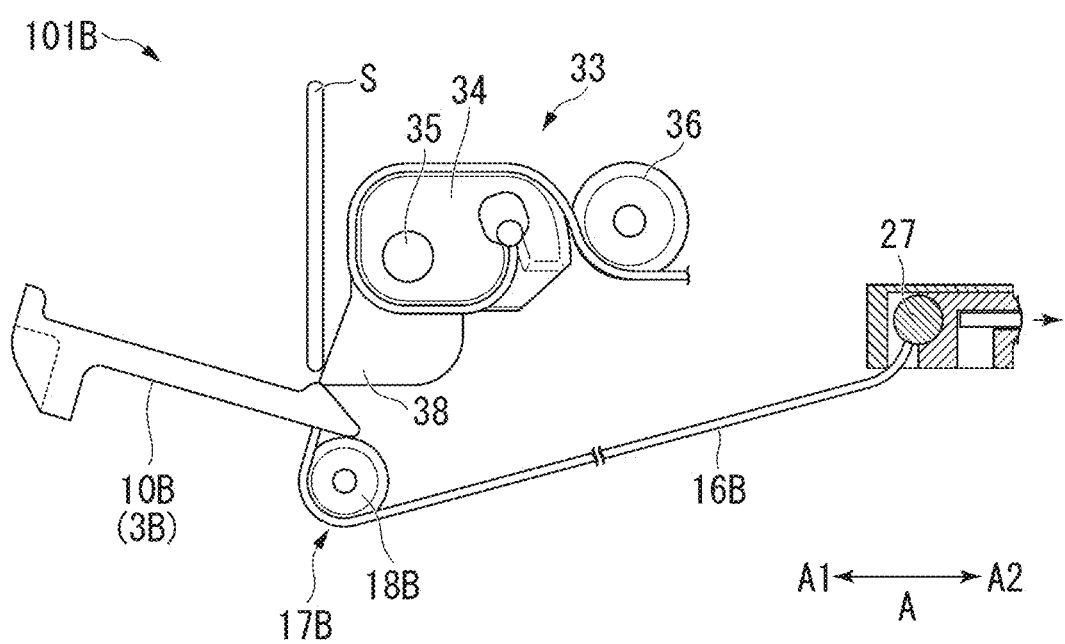
FIG. 24B is a view for explaining a schematic configuration and operation of the modified example of the medical stapler 100B of the second embodiment.

FIGS. 24A and 24B are views for explaining a schematic configuration and operation of a modified example of the medical stapler 100B of the second embodiment.

As illustrated in FIGS. 24A and 24B, a medical stapler 101B of a modified example of the second embodiment has a snap-fit operation part 17B. The snap-fit operation part 17B has a connection wire 16B and a third pulley 18B.

The connection wire 16B extends in the axial direction A, with one end side connected to the snap fit structure 10B and the other end side connected to the movable pin 27 described above. One end side of the connection wire 16B is connected to an end surface of the snap fit structure 10B on the downward direction B2 side. The third pulley 18B is disposed on the downward direction B2 side with respect to the snap fit structure 10B that locks onto the rotation member 33 (first pulley 34). The third pulley 18B is disposed at a position avoiding a displacement region of the snap fit structure 10B.

Thereby, even if the snap fit structure 10B is displaced due to rotation of the first pulley 34, the third pulley 18B interfering with the snap fit structure 10B can be avoided. One end side of the connection wire 16B is wound around the third pulley 18B from the downward direction B2 side by about half a turn, and the one end side of the connection wire 16B is folded back in the upward direction B1.

In the modified example of the second embodiment, when the gripping part 2 is in an open state as illustrated in FIG. 24A, the movable pin 27 is positioned at a most distal end side of a movable range thereof in the axial direction A, and the connection wire 16B is pushed out to the forward direction A1 side in the axial direction A. Since one end side of the connection wire 16B is folded back upward via the third pulley 18B, the snap fit structure 10B connected to the one end side of the connection wire 16B is pressed in the upward direction B1 and locks onto the first pulley 34 of the rotation member 33.

Also, when the gripping part 2 is in a closed state as illustrated in FIG. 24B, the movable pin 27 is positioned at a rearmost end side (rearward direction A2 side) of the movable range in the axial direction, and the connection wire 16B is pulled to the rear end side (the rearward direction A2 side). The snap fit structure 10B is placed in a state of being pulled to the downward direction B2 side by the connection wire 16B that has been pulled rearward, and the locking part 10b is separated from the first pulley 34. That is, the locking part 10b of the snap fit structure 10B is not locked onto the first pulley 34.

In this way, the connection wire 16B moves in the axial direction A as the gripping part 2 is opened and closed, and thereby engagement and disengagement of the snap fit structure 10B with the first pulley 34 are performed.

According to the modified example of the second embodiment, when the gripping part 2 is brought into an open state in the gripping step S15 described above, since the snap fit structure 10B locks onto the first pulley 34 of the rotation member 33, falling off of the staple S can be suppressed when the treatment target T is gripped by the gripping forceps G.

(Medical Stapler 100C of Third Embodiment)

Next, a medical stapler 100C of a third embodiment will be described.

The medical stapler 100C in the present embodiment is configured to prevent the staple S from being unintentionally ejected by restricting rotation of a rotation member 33 using a frictional force.

Figures 25, 26:
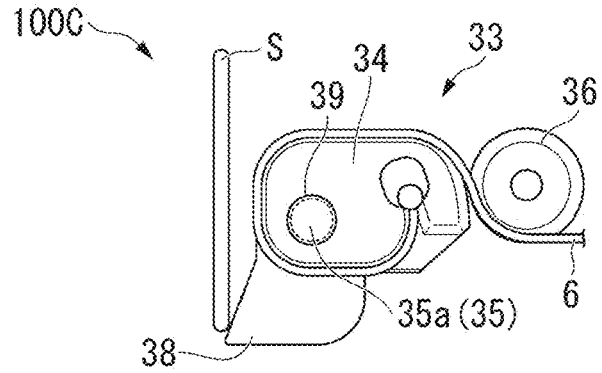
FIG. 25 is a view illustrating a configuration of a rotation member 33 of a medical stapler 100C according to a third embodiment.
FIG. 26 is a view illustrating a configuration of a medical stapler 100D according to a fourth embodiment.

FIG. 25 is a view illustrating a configuration of the rotation member 33 of the medical stapler 100C according to the third embodiment.

As illustrated in FIG. 25, the medical stapler 100C of the present embodiment includes a rotating shaft 35 as a structure to resist an unintended first tension applied to the ejection operation wire 6 due to curving deformation of the guide sheath. Both end parts 35a sides in the axial direction of the rotating shaft 35, which is integrated with a first pulley 34 of the rotation member 33, protrude from both sides of the first pulley 34 in the width direction and are supported by a first gripping member 21 of a staple ejection part 3 (see FIG. 9). The rotating shaft 35, together with the first pulley 34, rotates with respect to the first gripping member 21 of the staple ejection part 3.

In the present embodiment, a high friction part 39 is provided on each outer circumferential surface of both end parts 35a of the rotating shaft 35 to form a configuration that increases friction against the first gripping member 21. The high friction part 39 is not limited to the configuration of being provided at both end parts 35a of the rotating shaft 35, and may be provided on only one side.

The high friction part 39 in the present embodiment is made of a high-viscosity material layer formed of a resin material such as silicone rubber. Also, in this case, the rotating shaft 35 can be dipped in a resin liquid to form the high friction part 39 on an outer circumferential surface thereof.

Further, the high friction part 39 is not limited to being made of a high-viscosity material layer. For example, it may be formed of a material with properties other than high viscosity.

Due to the high friction part 39, a frictional force is generated between the end part 35a of the rotating shaft 35 and the first gripping member 21 of the staple ejection part 3. This frictional force is larger than the first tension described above and less than a pulling force (second tension) by the operator.

According to the present embodiment, even if an unintended first tension (a tension equal to or less than the pulling force applied by the operator) is generated in the ejection operation wire 6 when the endoscope 200 is inserted or removed or in a step other than the suturing step S17, a high friction force is generated between the rotating shaft 35 and a housing of the staple ejection part 3 due to the high friction part 39 provided on each outer circumferential surface of both end parts 35a of the rotating shaft 35, and the rotating shaft 35 (the first pulley 34) being easily rotated with respect to the housing of the staple ejection part 3 can be suppressed. In this way, since rotation of the first pulley 34 is restricted by the rotating shaft 35 which generates a frictional force against the first tension described above between itself and the housing of the staple ejection part 3, it is possible to suppress ejection of the staple S from the staple ejection part 3 due to unintended rotation of the first pulley 34.

Further, in the present embodiment, it has been configured such that the high friction part 39 is provided on each outer circumferential surface of both end parts 35a of the rotating shaft 35, but the present invention is not limited thereto. For example, the high friction part 39 may be provided on the housing side of the staple ejection part 3. Alternatively, the high-viscosity material layer may be provided on both the rotating shaft 35 side and the staple ejection part 3 side.

Also, as long as a high frictional force can be generated between the rotating shaft 35 and the housing of the staple ejection part 3, a material or the like of the high friction part can be changed as appropriate.

Also, an uneven portion may be provided as the high friction part 39 on at least one of an outer circumferential surface of the rotating shaft 35 and an inner circumferential surface of the insertion hole 21f (FIG. 9) through which the rotating shaft 35 is inserted in the first gripping member 21 of the staple ejection part 3. The uneven portion may be formed integrally with the outer circumferential surface of the end part 35a of the rotating shaft 35 or the inner circumferential surface of the insertion hole 21f described above, or may be a separate entity. Due to presence of the uneven portion between the outer circumferential surface of the end part 35a of the rotating shaft 35 and the inner circumferential surface of the insertion hole 21f in the first gripping member 21, a high frictional force can be generated between them.

(Medical Stapler 100D of Fourth Embodiment)

Next, a medical stapler 100D of a fourth embodiment will be described.

The medical stapler 100D of the present embodiment is configured to allow the wire itself to relieve tension by using an ejection operation wire 6D having a property of being extendable due to the first tension.

Figure 27:
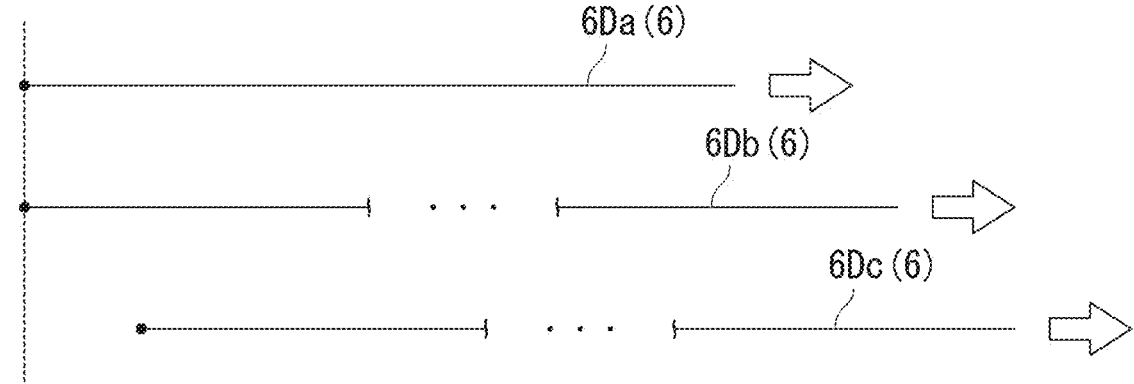
FIG. 27 is a diagram for explaining characteristics of an ejection operation wire 6D used in the medical stapler 100D of the fourth embodiment.
Figure 28:
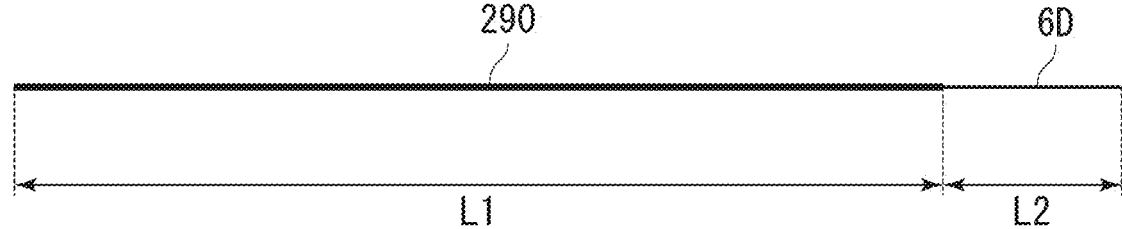
FIG. 28 is a diagram showing a difference in length between the ejection operation wire 6D and a guide sheath.

FIG. 26 is a view illustrating a configuration of the medical stapler 100D of the fourth embodiment. FIG. 27 is a diagram for explaining characteristics of the ejection operation wire 6D used in the medical stapler 100D of the fourth embodiment. FIG. 28 is a diagram showing a difference in length between the ejection operation wire 6D and a guide sheath.

As illustrated in FIG. 26, the medical stapler 100D of the present embodiment has the ejection operation wire 6D as a structure for absorbing an unintended first tension applied to the ejection operation wire 6D due to curving deformation of the guide sheath. As illustrated in FIG. 27, the ejection operation wire 6D is a wire in which an amount of elongation becomes saturated at a certain amount of tension. FIG. 27 shows an ejection operation wire 6 (6Da) at its initial length, an ejection operation wire 6 (6Db) in a state in which an amount of elongation has been saturated by the first tension, and an ejection operation wire 6 (6Dc) pulled backward by the second tension.

Such an ejection operation wire 6D is inserted through a flexible guide sheath (such as the resin sheath 290). As shown in FIG. 28, a length of the ejection operation wire 6D when the amount of elongation is saturated is larger than a length L1 of the guide sheath. The length of the ejection operation wire 6D when the amount of elongation is saturated is a length corresponding to a change in path of routing of the guide sheath, and is, for example, several millimeters (for example, 8 mm to 16 mm) longer than the guide sheath. A difference in length between the ejection operation wire 6D and the guide sheath (an amount of elongation L2 of the ejection operation wire 6D) is smaller than an amount of pulling of the ejection operation wire 6D due to the ejection operation unit 270.

According to the present embodiment, when the ejection operation wire 6D whose amount of elongation saturates at a certain amount of elongation is used, a change in the path length of the ejection operation wire 6D due to curvature of the guide sheath can be absorbed by the above-described amount of elongation (slack). Since the amount of saturated elongation in the ejection operation wire 6D is smaller than the amount of pulling of the ejection operation wire 6D by the ejection operation unit 270, it is possible to rotate the first pulley 34 of the rotation member 33 by pulling the ejection operation wire 6D.

Thereby, it is possible to suppress ejection of the staple S when an unintended amount of pulling force is applied to the ejection operation wire 6D (unintended pulling of the ejection operation wire 6D) due to curvature of the guide sheath.

Also, it is possible to prevent the staple S from being ejected when the ejection operation wire 6D is unintentionally pulled by the opening/closing operation wire 5 due to interference in the guide sheath between the opening/closing operation wire 5 and the ejection operation wire 6D of the gripping part 2.

Medical Stapler 100E of Fifth Embodiment

Next, a medical stapler 100E of a fifth embodiment will be described.

The medical stapler 100E of the present embodiment is configured to provide a bending for an ejection operation wire 6E in advance so that, when a first tension is applied, the tension can be alleviated by the amount of bending of the ejection operation wire 6E.

Figure 29:
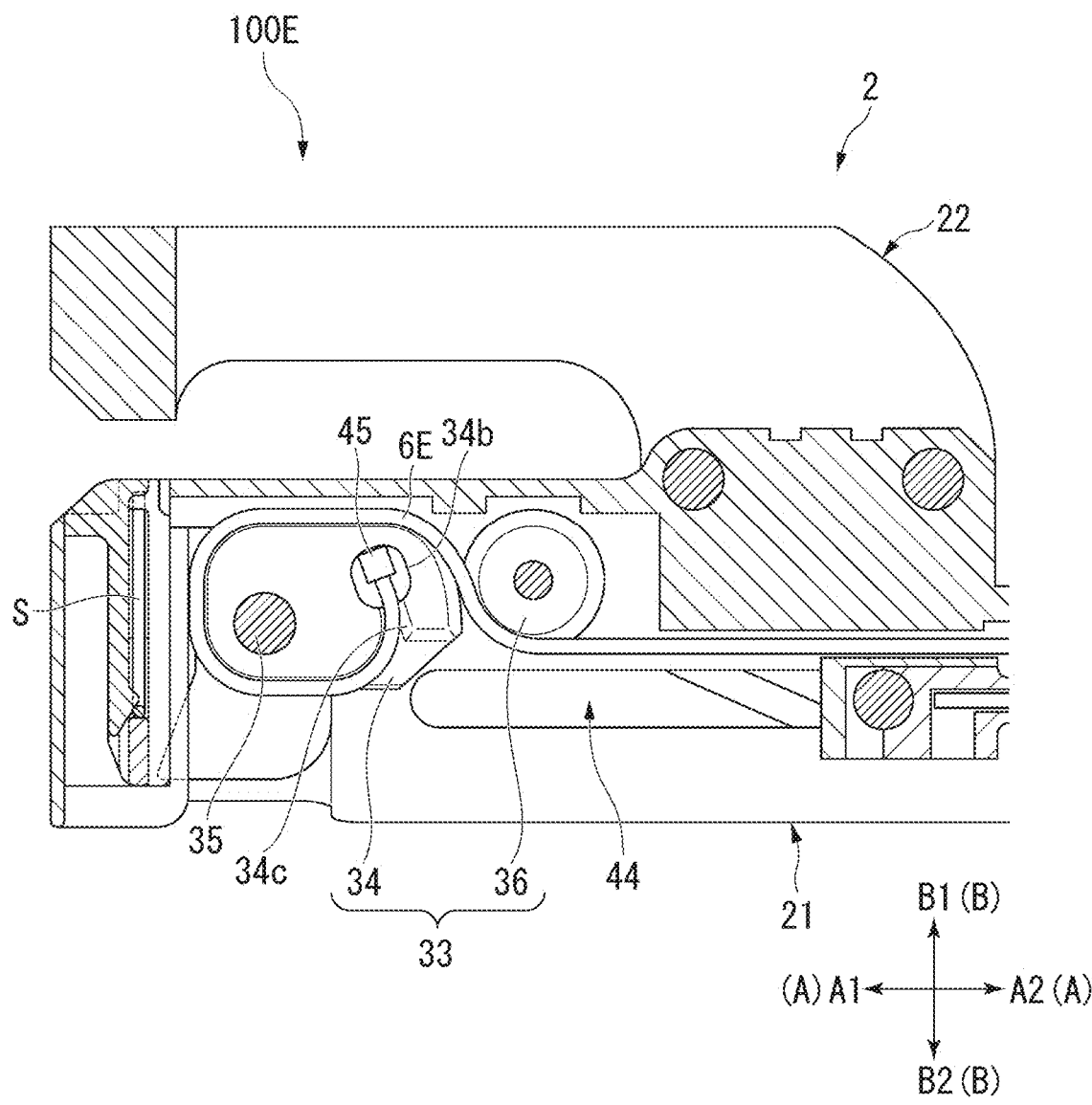
FIG. 29 is a view for explaining a configuration, and effects of a medical stapler 100E of a fifth embodiment.
Figure 30:
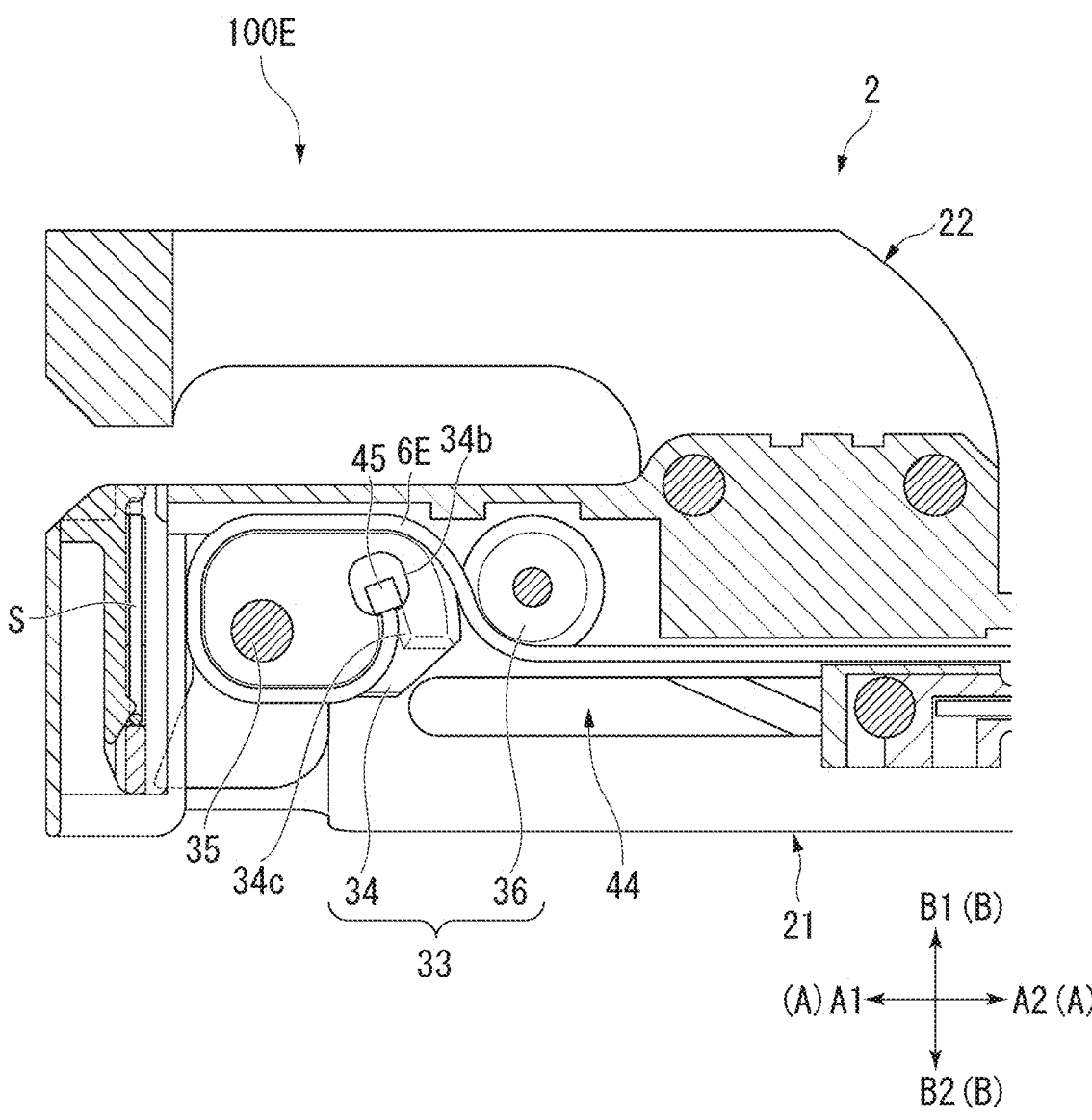
FIG. 30 is a view for explaining a configuration, and effects of the medical stapler 100E of the fifth embodiment.

FIGS. 29 and 30 are views for explaining a configuration, and effects of the medical stapler 100E of the fifth embodiment.

As illustrated in FIG. 29, the medical stapler 100E of the present embodiment has a tension absorbing structure (ejection restriction structure) 44 as a structure for absorbing an unintended first tension applied to the ejection operation wire 6E due to curving deformation of the guide sheath. The tension absorbing structure 44 is constituted by a first pulley 34 of a rotation member 33, the ejection operation wire 6E connected to the first pulley 34, and a connector 45 connecting the first pulley 34 and the ejection operation wire 6E.

The first pulley 34 includes a connection hole 34b to which the ejection operation wire 6E is connected via the connector 45, and a guide groove 34c formed on an outer circumference around an axis of a rotating shaft 35. The guide groove 34c communicates with the connection hole 34b. A distal end side of the ejection operation wire 6E is wound around the first pulley 34 along the guide groove 34c formed on the outer circumference.

A most distal end of the ejection operation wire 6E is connected to the first pulley 34 of the rotation member 33 via the connector 45. The connector 45 is provided at the distal end of the ejection operation wire 6E. The connector 45 has a diameter larger than a diameter of the ejection operation wire 6E, and also has a diameter larger than a groove width of the guide groove 34c formed in the first pulley 34. Thereby, the connector 45 functions as a retainer for preventing the ejection operation wire 6E from coming off from the first pulley 34 by locking onto a boundary portion between the connection hole 34b and the guide groove 34c of the first pulley 34.

When the ejection operation wire 6E is not being pulled with respect to the gripping part 2 in a closed state, the distal end side of the ejection operation wire 6E is inserted into the back of the connection hole 34b of the first pulley 34, and the connector 45 is in a state of not being locked onto the first pulley 34. That is, the connector 45 is disposed at an initial position at the back of the connection hole 34b, and is spaced apart from the boundary between the connection hole 34b and the guide groove 34c. In this way, in a state in which the ejection operation wire 6E is not pulled, a certain distance (allowance) is secured between the connector 45, which is provided at the distal end of the ejection operation wire 6E, and the first pulley 34.

Thereby, when an unintended first tension (a tension equal to or less than a pulling force (second tension) by the operator) acts on the ejection operation wire 6E due to curvature of the guide sheath, the connector 45, which has been positioned at the back side in the connection hole 34b of the first pulley 34, moves. The connector 45 moves by a certain distance in a direction in which the ejection operation wire 6E extends, and then locks onto the boundary portion between the connection hole 34b and the guide groove 34c.

A position at which the connector 45 locks onto the boundary portion between the connection hole 34b and the guide groove 34c is defined as a "connection position" according to the present invention. Thereby, the ejection operation wire 6E is placed in a state of being coupled to the first pulley 34.

Thereafter, when the wire sheath operation unit 260 is operated by the operator to pull the ejection operation wire 6E coupled to the first pulley 34 via the connector 45, and a pulling force (second tension) equal to or more than the first tension described above is applied to the ejection operation wire 6E, the first pulley 34, which is in a connected state to the ejection operation wire 6E, rotates around the axis of the rotating shaft 35, and the staple S is ejected at a timing intended by the operator. In this way, the suturing step S17 can be performed on the treatment target T.

According to the configuration of the present embodiment, during a state in which the wire sheath operation unit 260 is not operated by the operator (a state in which the ejection operation wire 6E is not pulled), even if an unintended first tension (first tension: a tension equal to or less than a pulling force by the operator) acts on the ejection operation wire 6E due to curvature of the guide sheath, since the connector 45 (ejection operation wire 6E) disposed at the "initial position" is in a state of not locking onto the first pulley 34, it is possible to absorb movement of the ejection operation wire 6E to the "connection position" at which the connector 45 locks onto the first pulley 34. Thereby, it is possible to suppress rotation of the first pulley 34 when the ejection operation wire 6E is not pulled by the operator, and to prevent the staple S from being ejected at a timing not intended by the operator.

Medical Stapler 100F of Sixth Embodiment

Next, a medical stapler 100F according to a sixth embodiment will be described.

The medical stapler 100F of the present embodiment has a configuration in which a second pulley 36F supporting the ejection operation wire is made variable so that the second pulley 36F moves in accordance with a tension applied to the ejection operation wire to alleviate a first tension.

Figure 31:
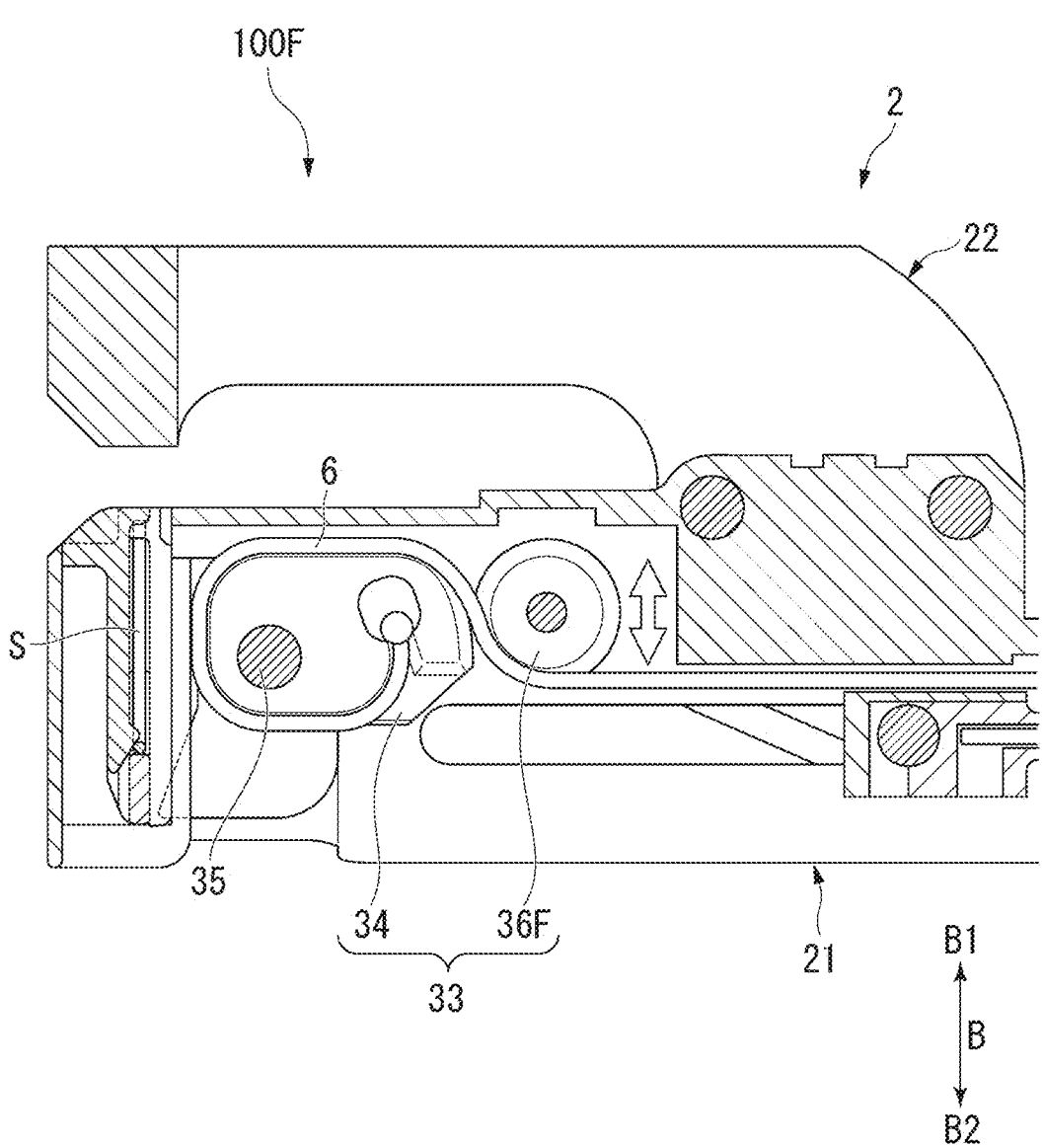
FIG. 31 is a view for explaining a configuration, and effects of a medical stapler 100F of a sixth embodiment.
Figure 32:
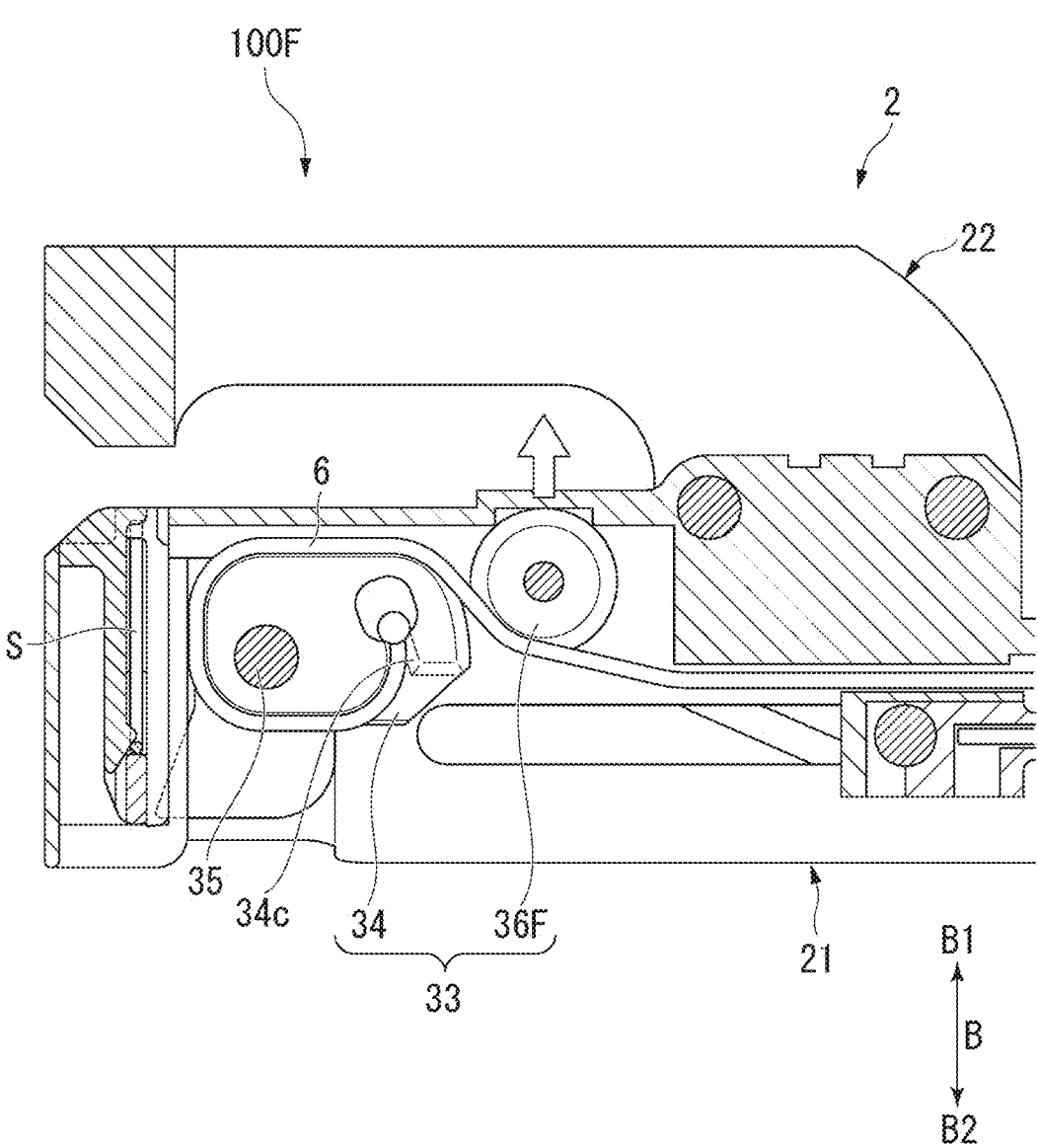
FIG. 32 is a view for explaining a configuration, and effects of the medical stapler 100F of the sixth embodiment.

FIGS. 31 and 32 are views for explaining a configuration, and effects of the medical stapler 100F of the sixth embodiment.

As illustrated in FIG. 31, the medical stapler 100F of the present embodiment has a displacement-type second pulley (second member) 36F as a structure for absorbing an unintended first tension (a tension equal to or less than a pulling force by the operator) applied to the ejection operation wire 6 due to curving deformation of the guide sheath. The displacement-type second pulley 36F is formed of a movable pulley and is movable in the vertical direction B as illustrated in FIGS. 31 and 32. The displacement-type second pulley 36F moves in the upward direction B1 according to a magnitude of the tension applied to the ejection operation wire 6. In the present embodiment, the displacement-type second pulley 36F rises to a position of alleviating the first tension applied to the ejection operation wire 6 (hereinafter referred to as a "tension alleviation position"). That is, the displacement-type second pulley 36F rises to a position that does not significantly hinder the ejection operation wire 6 from becoming straight, thereby functioning to suppress rotation of the first pulley 34 due to the first tension.

An upper limit position of the displacement-type second pulley 36F is preferably a position at which the ejection operation wire 6 can be guided (supported) with a force that does not resist the first tension applied to the ejection operation wire 6.

On the other hand, a lower limit position of the displacement-type second pulley 36F is preferably a position that can support the ejection operation wire 6 so that a position of a rear end portion of the ejection operation wire 6 inserted through the guide sheath is an initial position with respect to the guide sheath when there is no bending in the guide sheath and no unnecessary tension is applied to the ejection operation wire 6.

According to the present embodiment, during a state in which the wire sheath operation unit 260 (FIG. 1) is not operated by the operator (a state in which the ejection operation wire 6 is not pulled), even if an unintended first tension acts on the ejection operation wire 6 due to curvature of the guide sheath, the first tension applied to the ejection operation wire 6 can be absorbed when the second pulley 36F that guides the ejection operation wire 6 is displaced in the upward direction B1. Thereby, it is possible to suppress rotation of the first pulley 34 when the ejection operation wire 6 is not pulled by the operator, and to prevent the staple S from being ejected at a timing not intended by the operator.

Further, in the present embodiment, the second member according to the present invention is configured to include the displacement-type second pulley 36F, but the second member may be configured to not rotate.

Medical Stapler 100G of Seventh Embodiment

Next, a medical stapler 100G according to a seventh embodiment will be described.

The medical stapler 100G of the present embodiment is configured to include a snap fit part 133 that restricts movement of a linear moving member 32G by coming into contact with the linear moving member 32G that supports a staple S.

Figure 33:
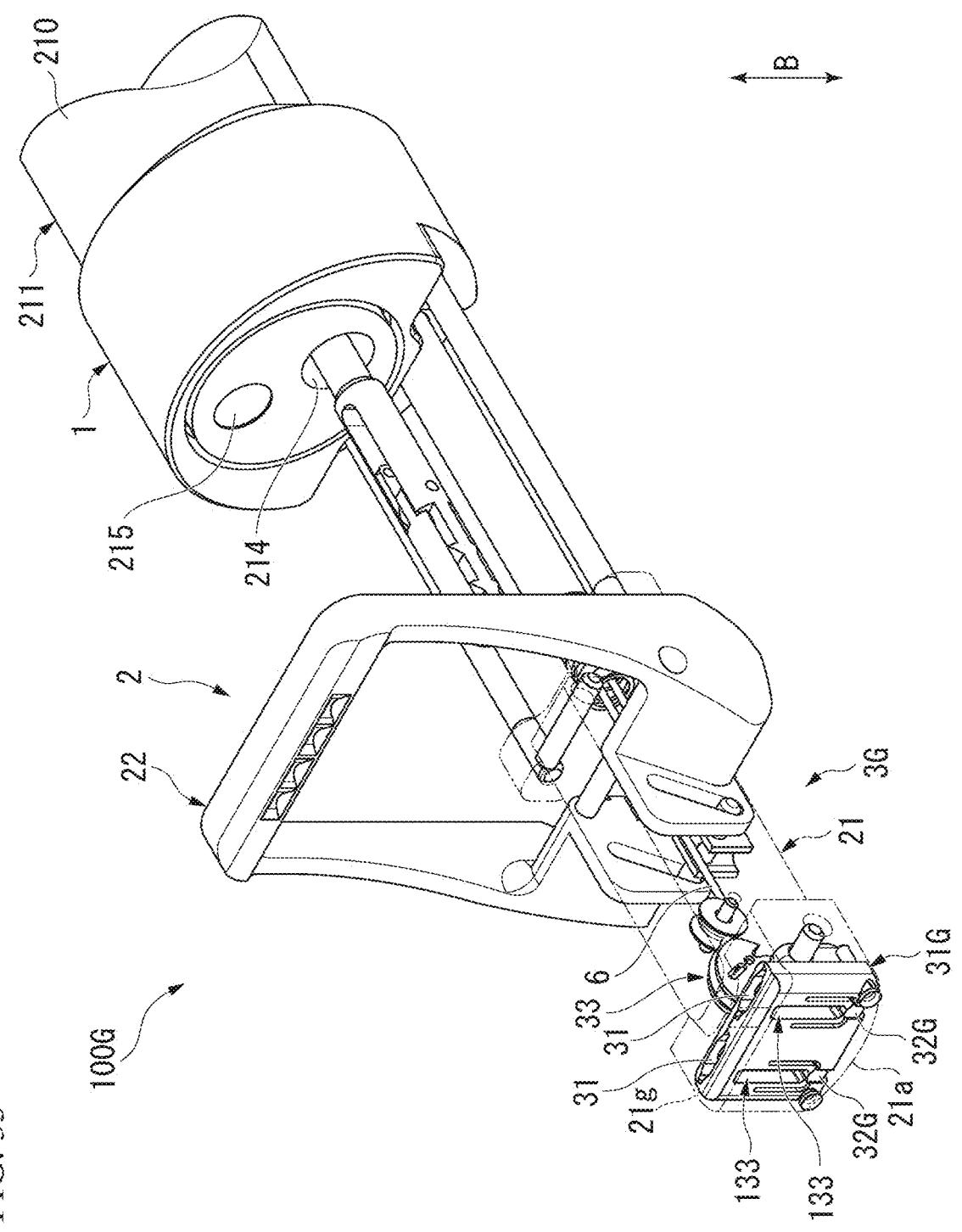
FIG. 33 is a perspective view illustrating a configuration of a medical stapler 100G according to a seventh embodiment.
Figure 34:
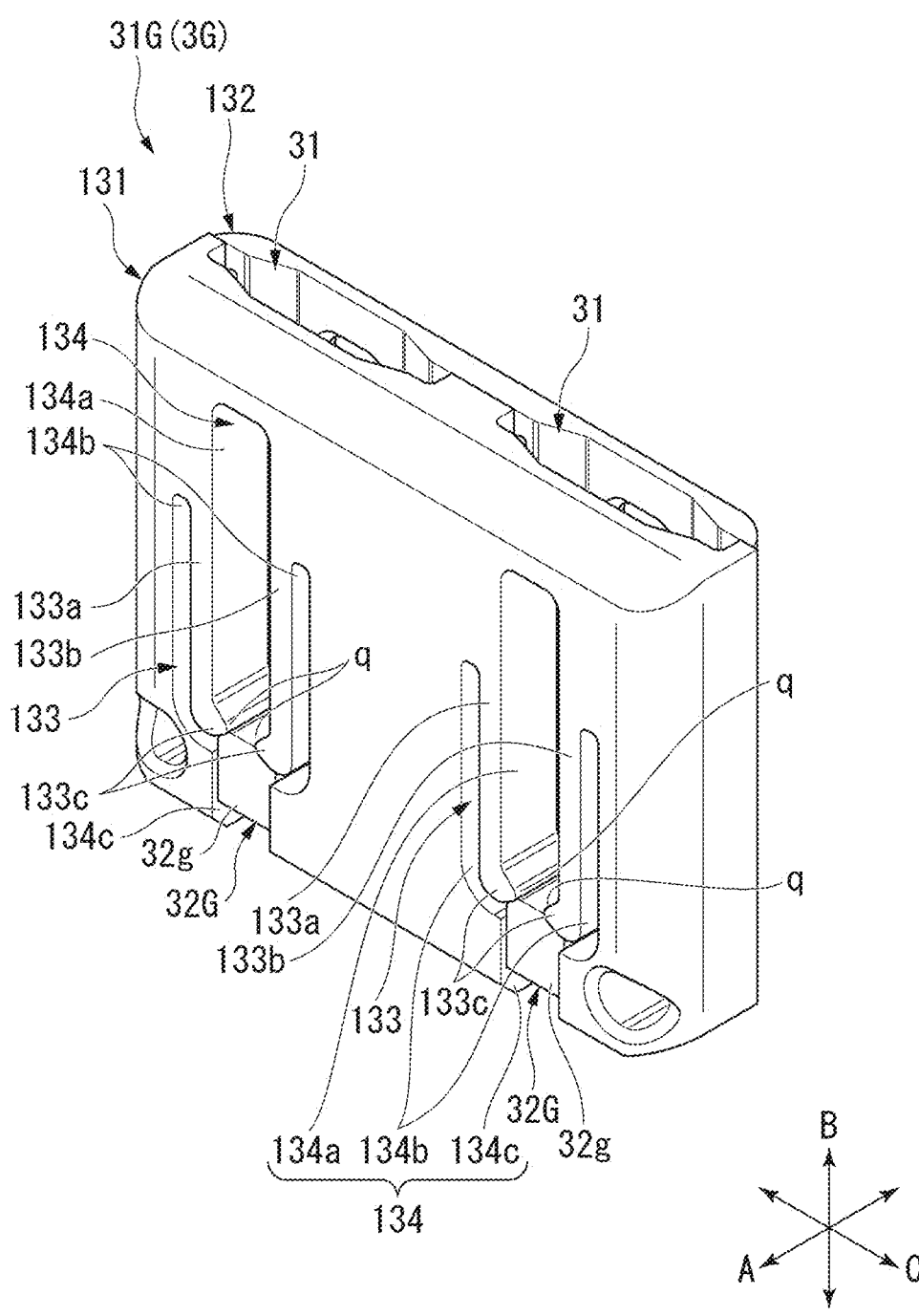
FIG. 34 is a perspective view illustrating a configuration of a storage housing 31G in a staple ejection part 3G.
Figure 35:
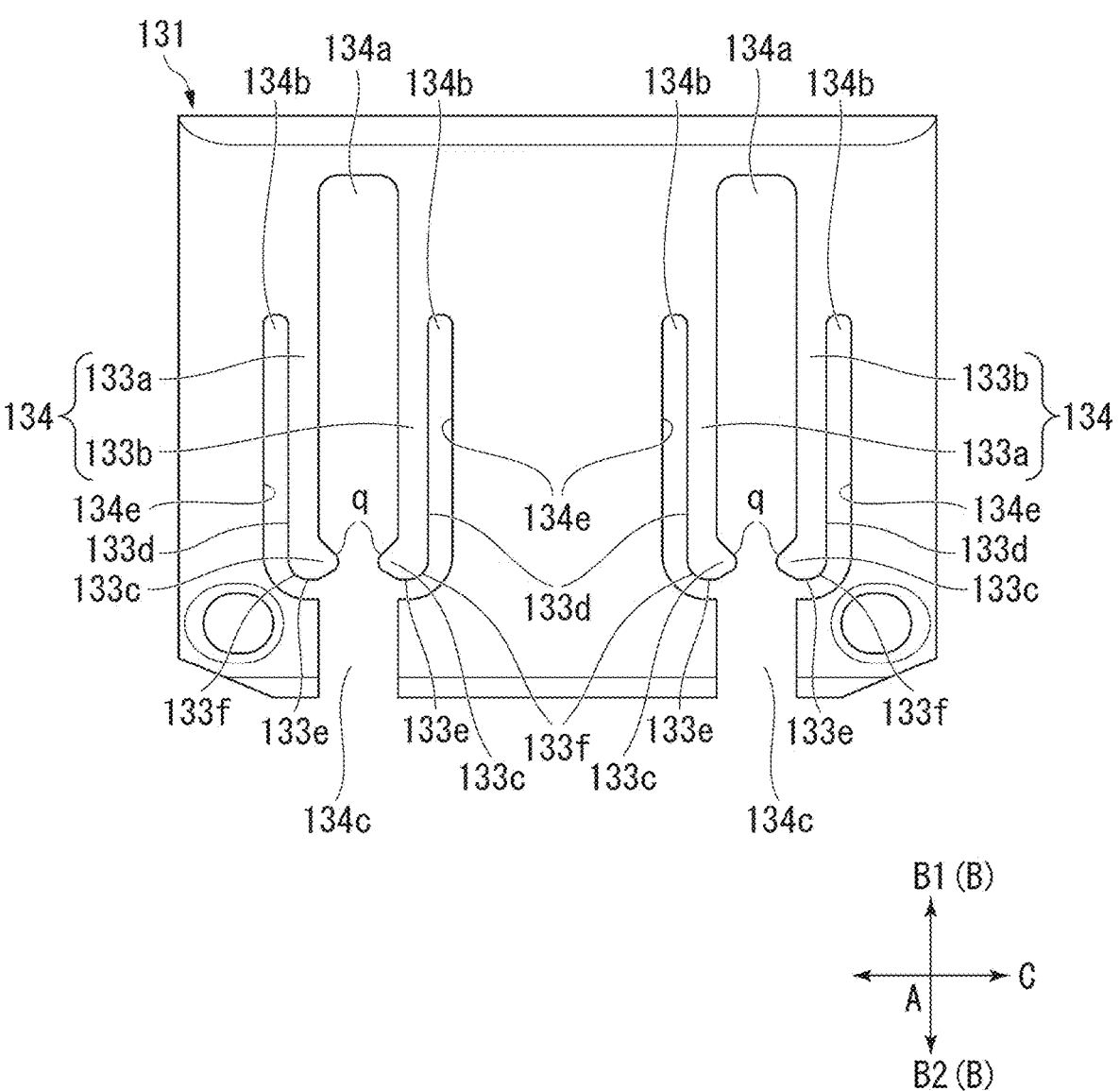
FIG. 35 is an exploded perspective view illustrating a configuration of the storage housing 31G in the staple ejection part 3.
Figure 36:
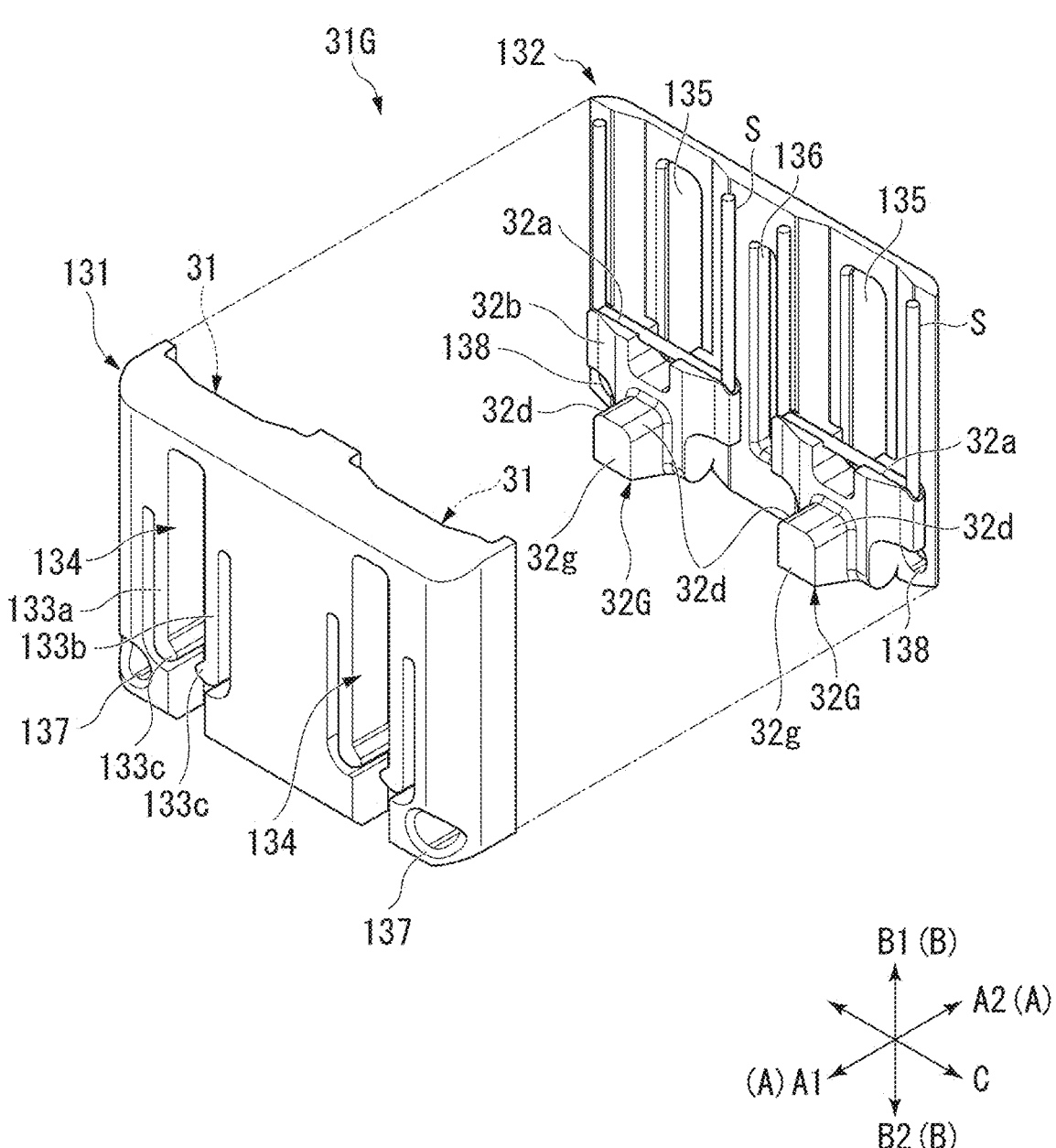
FIG. 36 is an exploded perspective view illustrating a configuration of the storage housing 31G in the staple ejection part 3.
Figure 37:
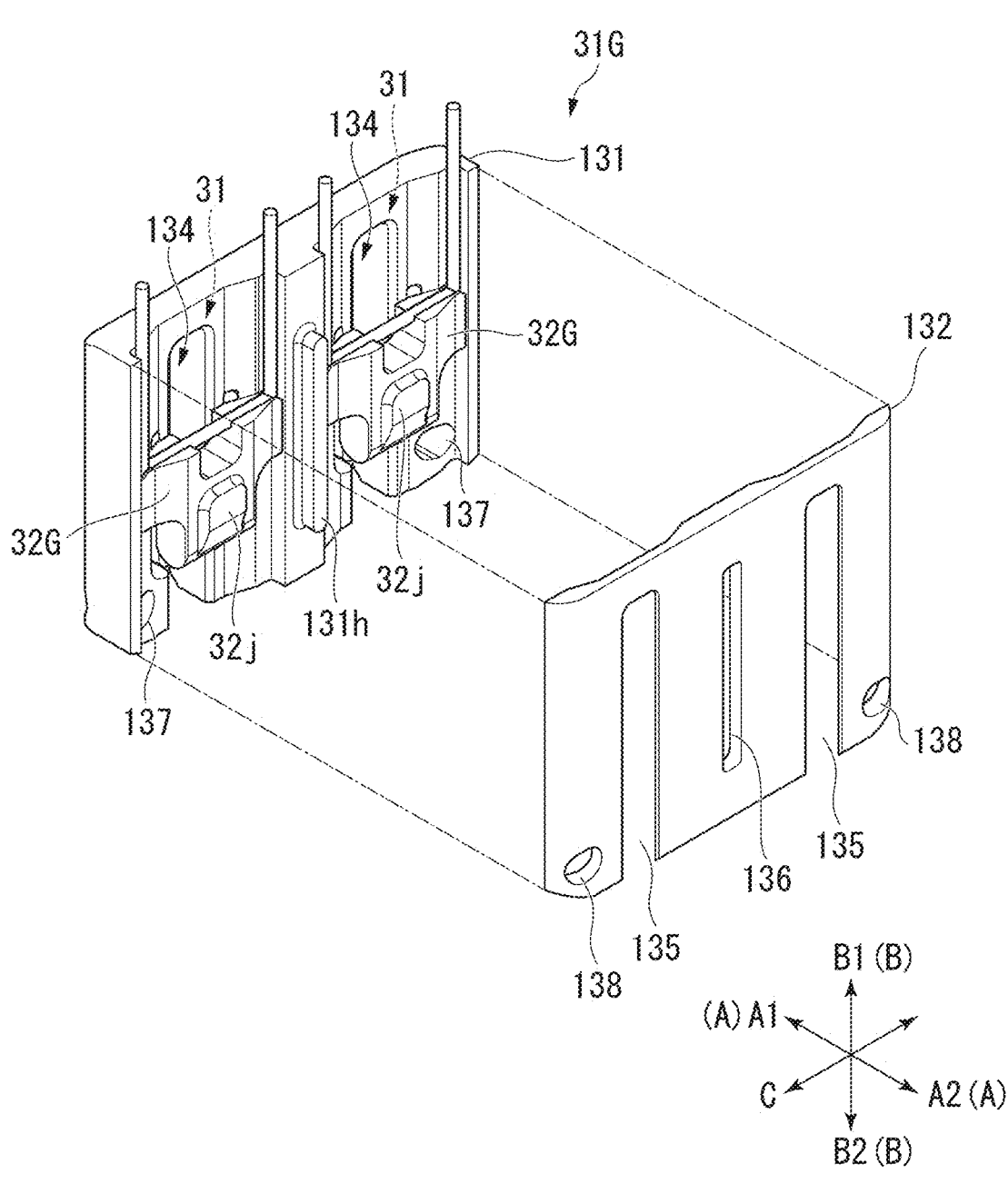
FIG. 37 is a front view illustrating a configuration of a first member 131 of the storage housing 31G.

FIG. 33 is a perspective view illustrating a configuration of the medical stapler 100G of the seventh embodiment. FIG. 34 is a perspective view illustrating a configuration of a storage housing 31G in a staple ejection part 3G. FIGS. 35 and 36 are exploded perspective views illustrating a configuration of the storage housing 31G in the staple ejection part 3. FIG. 37 is a front view illustrating a configuration of a first member 131 of the storage housing 31G.

As illustrated in FIG. 33, the medical stapler 100G of the present embodiment includes a staple ejection part 3G that can resist an unintended first tension applied to the ejection operation wire 6 due to curving deformation of the guide sheath.

The staple ejection part 3G includes the storage housing 31G having a staple storage part 31, the linear moving member 32G, and a rotation member 33. The storage housing 31G is a member incorporated in a first distal end part 21a of a first gripping member 21 and is separate from the first gripping member 21. Further, the present invention is not limited to this configuration, and the storage housing 31G may be configured integrally with the first gripping member 21.

The storage housing 31G is inserted into a recessed part 21g formed in the first distal end part 21a of the first gripping member 21 and an upper surface of the storage housing 31G coincides with an upper surface of the first distal end part 21a. The storage housing 31G has a pair of staple storage parts 31 in the width direction C, and the staple S (not illustrated in FIG. 33) is inserted into each of the staple storage parts 31. A linear moving member 32G supporting the staple S is disposed in each staple storage part 31 of the storage housing 31G. The linear moving member 32G supports the staple S inserted in the staple storage part 31 from below and moves it in the vertical direction B.

As illustrated in FIG. 34, the storage housing 31G is constituted by the first member 131 and a second member 132.

As illustrated in FIG. 35, the first member 131 has the pair of snap fit parts 133 and a pair of through holes 134 at positions corresponding to the pair of staple storage parts 31.

The snap fit part 133 has a pair of snap fit structures 133a and 133b formed at a predetermined distance in the width direction C. The pair of snap fit structures 133a and 133b have a thin rod shape extending in the vertical direction B, and have locking parts 133c formed on the downward direction B2 side to protrude in directions facing each other in the width direction C. The locking part 133c has a triangular shape when viewed from the axial direction A, and an apex q protruding most in the width direction C is made to have a non-sharp shape. Both outer sides of the locking parts 133c in the width direction C are chamfered, and a connecting surface 133f connecting an outer surface 133d on an outer side in the width direction C and a lower end surface 133e is formed into a smooth curved surface.

The through hole 134 penetrates the first member 131 in a thickness direction. The through hole 134 has a first through hole 134a formed between the pair of snap fit structures 133a and 133b, second through holes 134b formed on both outer sides of the pair of snap fit structures 133a and 133b in the width direction C, and a third through hole 134c formed on a lower end side of the pair of snap fit structures 133a and 133b. The first through hole 134a is formed to be longer in the vertical direction B than the second through hole 134b. An upper end side of the first through hole 134a does not reach an upper surface of the storage housing 31G. A lower end side of the first through hole 134a communicates with the third through hole 134c. The second through holes 134b communicate with the first through hole 134a and the third through hole 134c from both sides of them in the width direction C below the pair of snap fit structures 133a and 133b in the downward direction B2. The third through hole 134c, which communicates with the first through hole 134a in the vertical direction B, opens at a lower surface of the first member 131.

The first through hole 134a and the third through hole 134c are guide holes that guide the inserted linear moving member 32G in the vertical direction B. A combined length of the first through hole 134a and the third through hole 134c in the vertical direction B is equal to or slightly larger than a movement range of the linear moving member 32G in the vertical direction B.

The second through holes 134b are through holes that form gaps to allow displacement of the pair of snap fit structures 133a and 133b to both sides in the width direction C. The second through holes 134b have a length in the vertical direction B that is smaller than that of the first through hole 134a. A width of the second through holes 134b in the width direction C is substantially equal to or slightly smaller than a width of the snap fit structures 133a and 133b. A width of the pair of second through holes 134b is preferable that when the linear moving member 32 passes between the locking parts 133c of the pair of snap fit structures 133a and 133b, the snap fit structures 133a and 133b displaced to both sides in the width direction do not come into contact with inner surfaces 134e of each second through hole 134b.

A protrusion 32g of the linear moving member 32G as illustrated in FIGS. 34 and 36 is inserted into the third through hole 134c. The protrusion 32g is a prism-shaped protruding part that protrudes in the forward direction A1 from a support part 32b that supports the staple S, and comes into contact with lower ends of the pair of snap fit structures 133a and 133b from the downward direction B2 side. The above-described recessed part 32a into which the staple S is fitted is formed on an upper surface of the support part 32b.

The support part 32b of the linear moving member 32 has a substantially square shape when viewed from the forward direction A1 side, and a pair of corners on the upward direction B1 side are chamfered with an R shape. A pair of R surfaces 32d of the support part 32b respectively come into contact with the locking parts 133c of the snap fit structures 133a and 133b, which are positioned on a side in the upward direction B1, from the downward direction B2 side. A dimension of the protrusion 32g in the width direction C when viewed from the axial direction A is set to be larger than a distance between the locking parts 133c of the pair of snap fit structures 133a and 133b. Thereby, the protrusion 32g comes into contact with the locking parts 133c of the pair of snap fit structures 133a and 133b. A protruding length of the protrusion 32g in the axial direction A is substantially equal to a plate thickness of the snap fit structures 133a and 133b. Further, the protruding length of the protrusion 32g in the axial direction A and the plate thickness of the snap fit structures 133a and 133b may have different dimensions as long as rigidity of both can be secured.

As illustrated in FIGS. 36 and 37, the second member 132 is disposed on the rearward direction A2 side of the first member 131. The second member 132 has a pair of through holes 135 and a positioning hole 136 formed between the pair of through holes 135 at positions corresponding to the pair of staple storage parts 31.

The through holes 135 are formed at positions facing the through holes 134 of the first member 131 in the axial direction A. The through holes 135 each penetrate the second member 132 in a thickness direction. The through hole 135 is formed long in the vertical direction B, and is substantially equal to a combined length of the first through hole 134a and the third through hole 134c of the first member 131. The through hole 135 opens at a lower surface of the second member 132. Into such a through hole 135, a protrusion 32j protruding in the rearward direction A2 from a rear surface of the linear moving member 32G is inserted as illustrated in FIG. 37.

The positioning hole 136 is a long hole that is narrower and shorter than the through hole 135 and is formed in the vertical direction B. The positioning hole 136 is formed at substantially a center of the second member 132 in the vertical and horizontal directions. A positioning protruding part 131h formed on an inner surface of the first member 131 (a surface on the rearward direction A2 side facing the second member 132) is inserted into the positioning hole 136. The positioning hole 136 is formed to be slightly larger than the positioning protruding part 131h.

The first member 131 and the second member 132 are fixed together via connection members (not illustrated) inserted into a pair of insertion holes 137 formed on a lower end side of the first member 131 and a pair of insertion holes 138 formed on a lower end side of the second member 132. When the first member 131 and the second member 132 are assembled, positioning of both members can be easily achieved by combining them while inserting the positioning protruding part 131h of the first member 131 into the positioning hole 136 of the second member 132, thereby reducing the time and effort required for assembly.

Next, effects of the medical stapler 100G of the seventh embodiment will be described.

Figure 38:
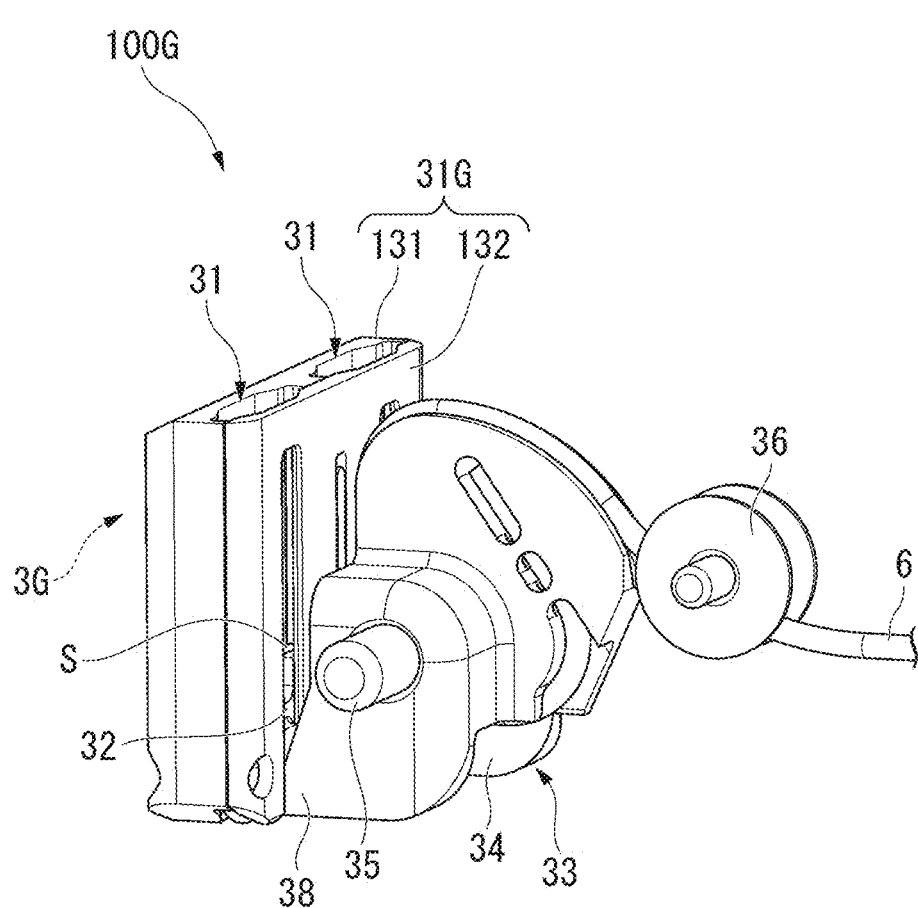
FIG. 38 is a perspective view illustrating a peripheral structure of the staple ejection part 3G of the medical stapler 100G as viewed obliquely from behind.
Figure 39:
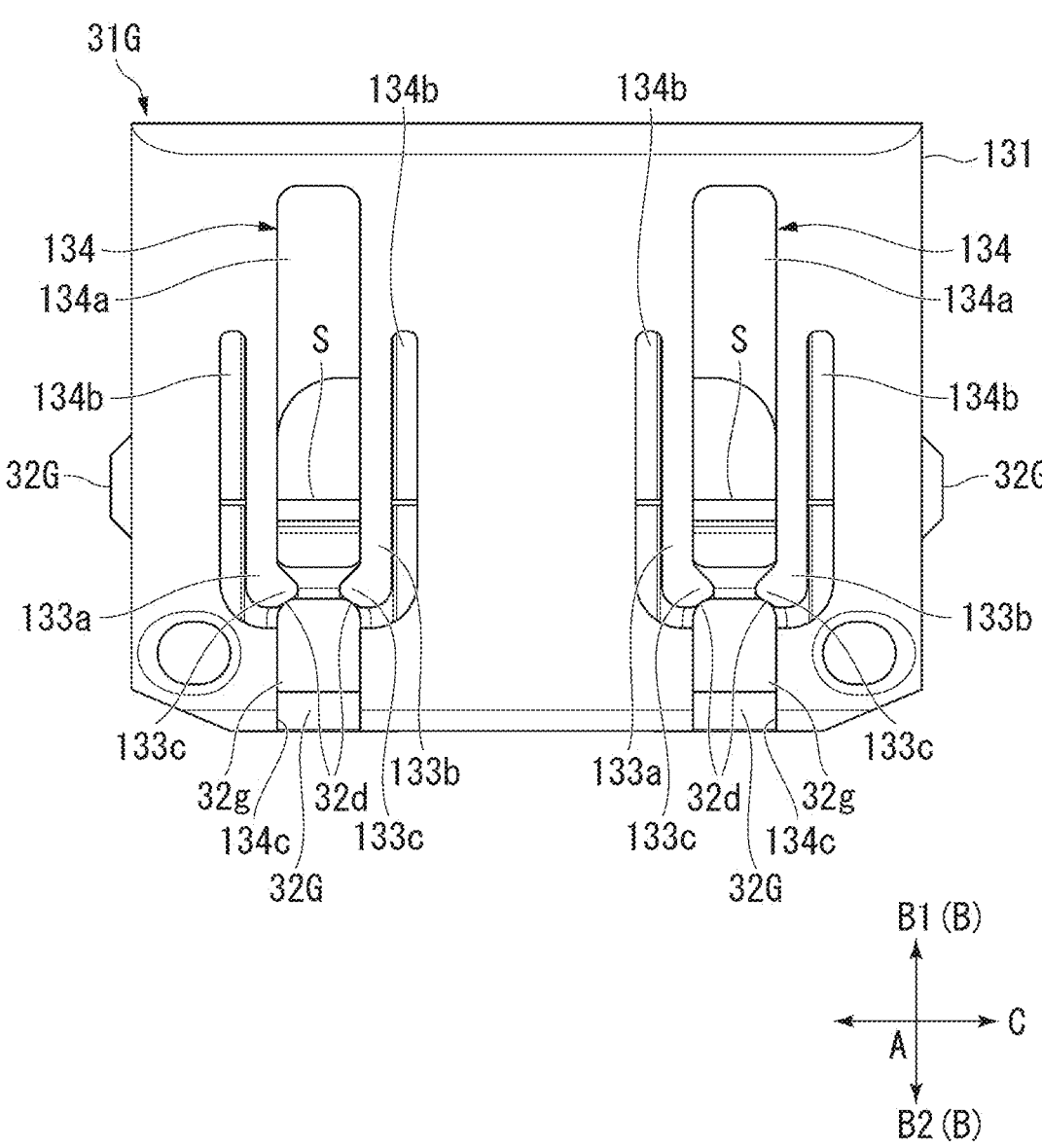
FIG. 39 is a front view of the staple ejection part 3G of the medical stapler 100G from a forward direction A1 side.
Figure 40:
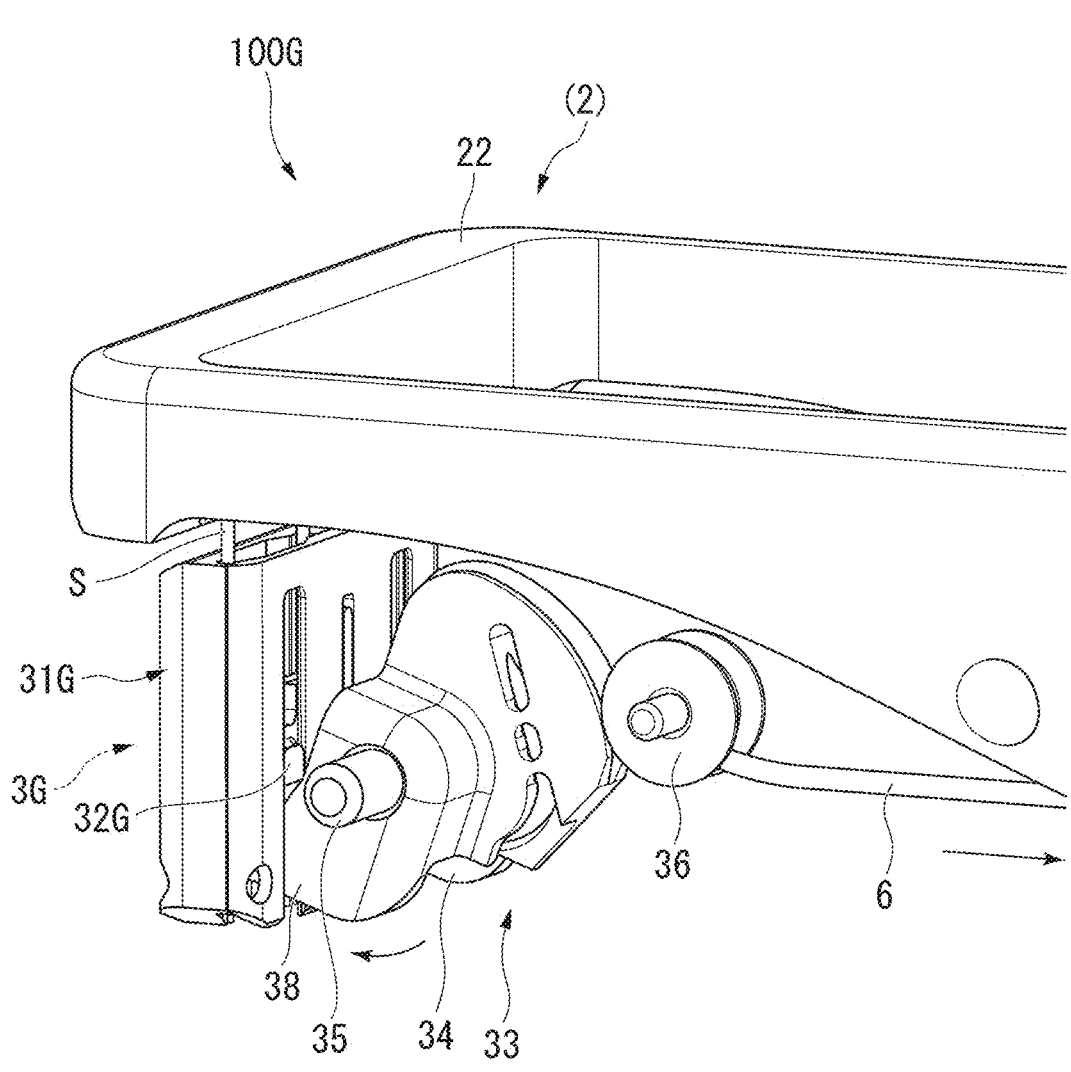
FIG. 40 is a perspective view illustrating a peripheral structure of the staple ejection part 3G of the medical stapler 100G as viewed obliquely from behind.
Figure 41:
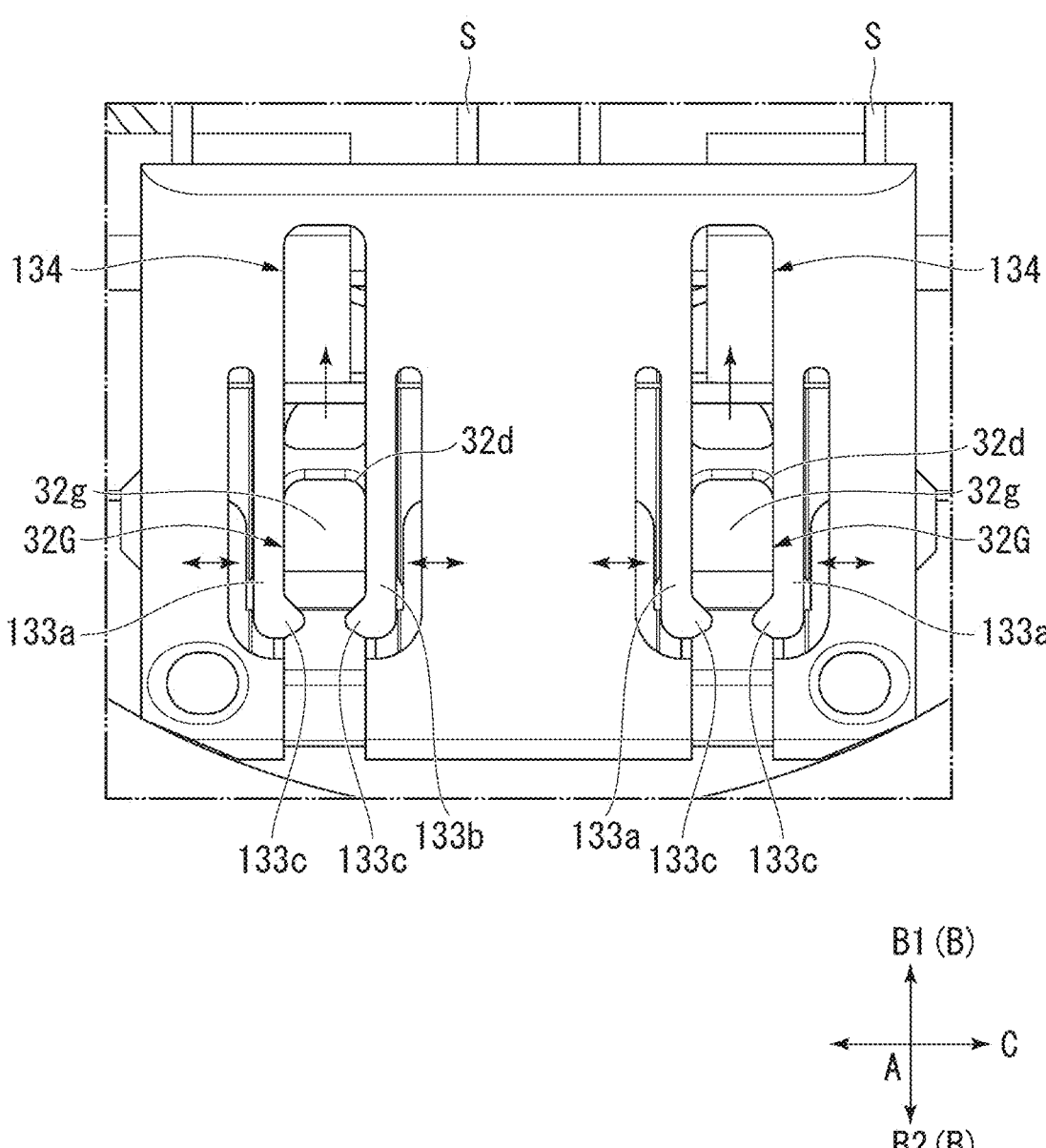
FIG. 41 is a front view of the staple ejection part 3G of the medical stapler 100G from the forward direction A1 side.
Figure 42:
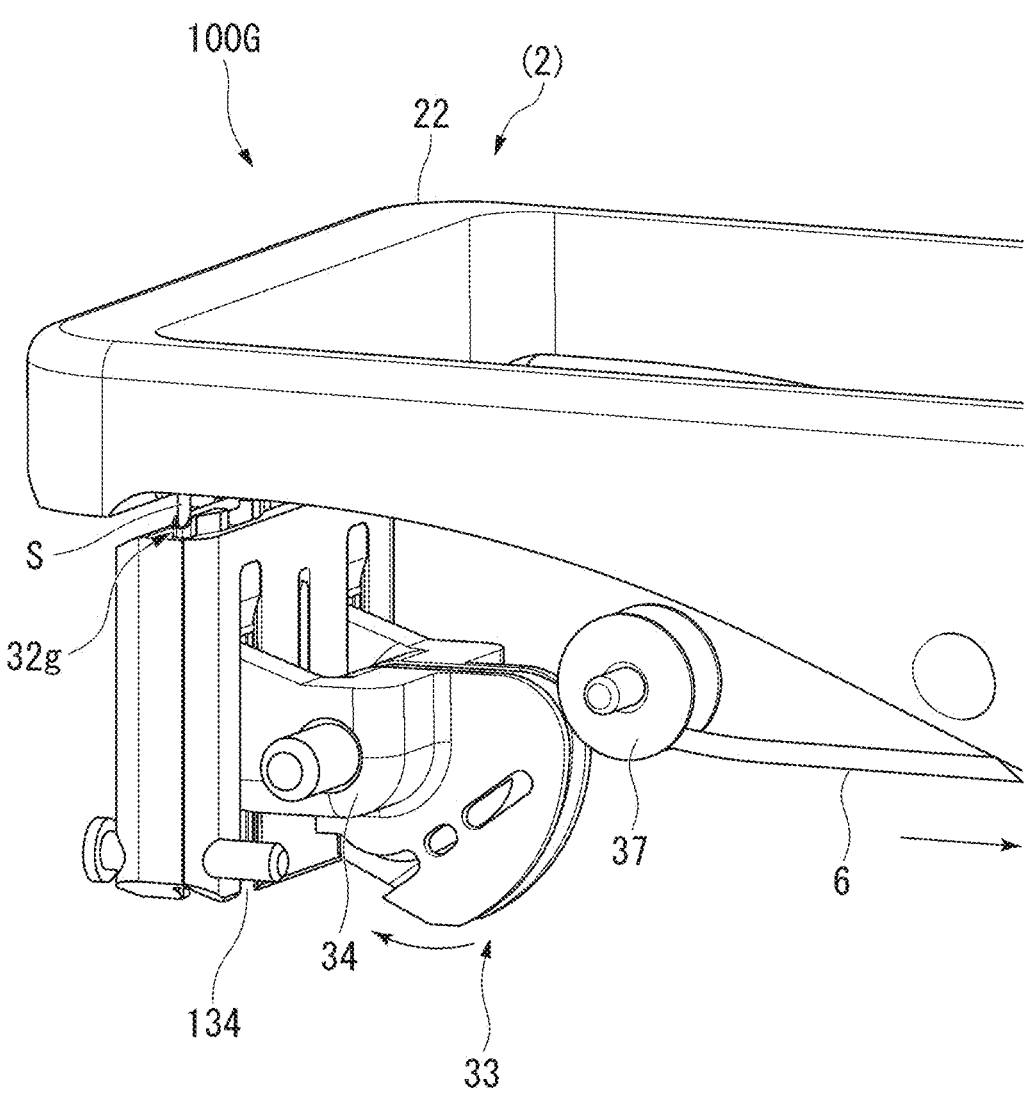
FIG. 42 is a perspective view illustrating a peripheral structure of the staple ejection part 3G of the medical stapler 100G as viewed obliquely from behind.
Figure 43:
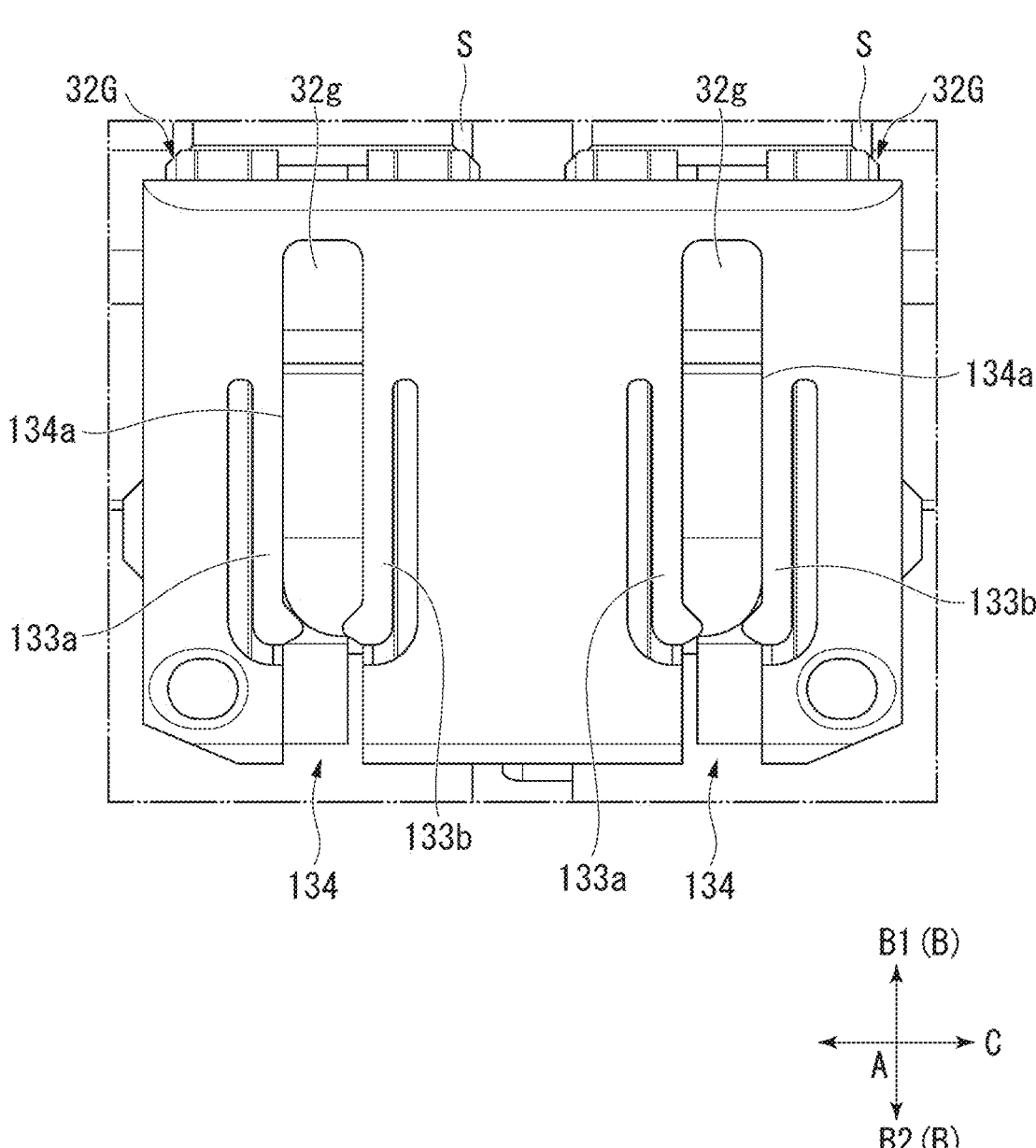
FIG. 43 is a front view of the staple ejection part 3G of the medical stapler 100G from the forward direction A1 side.

FIGS. 38, 40, and 42 are perspective views illustrating a peripheral structure of the staple ejection part 3G of the medical stapler 100G as viewed obliquely from behind. FIGS. 39, 41, and 43 are front views of the staple ejection part 3G of the medical stapler 100G from the forward direction A1 side.

FIGS. 38 and 39 illustrate a state (initial state) in which the ejection operation wire 6 is not pulled by the operator.

As illustrated in FIGS. 38 and 39, in a state in which the ejection operation wire 6 is not pulled by the operator, substantially the entirety of the pair of staples S inserted into the storage housing 31G is stored without being exposed from the upper surface of the storage housing 31G. A pair of linear moving members 32G (the protrusions 32g) respectively supporting the pair of staples S from below come into contact with the locking parts 133c of the pair of snap fit structure parts 133 provided in the first member 131 of the storage housing 31G. At this time, the pair of R surfaces 32d of the protrusion 32g of the linear moving member 32G come into contact with the locking parts 133c of the snap fit structures 133a and 133b, respectively.

In such an initial state, for example, even if an unintended first tension is applied to the ejection operation wire 6 due to curvature of the guide sheath, when the tension is equal to or less than a certain amount of pulling force (second tension), the linear moving member 32G remains in contact with the snap fit structures 133a and 133b and does not rise any further, and the snap fit structures 133a and 133b are not displaced outward on both sides in the width direction C. In this manner, the snap fit structures 133a and 133b hold the upwardly movable linear moving member 32G in its initial position.

FIGS. 40 and 41 illustrate a state immediately after the ejection operation wire 6 is pulled by the operator.

As illustrated in FIGS. 40 and 41, when the ejection operation wire 6 is pulled by the operator, the first pulley 34 connected to the ejection operation wire 6 rotates, and the linear moving member 32G is pushed up. At this time, if the first pulley 34 is further rotated when the ejection operation wire 6 is pulled with a force equal to or more than a certain level, the linear moving member 32G rises while pushing the pair of snap fit structures 133a and 133b to both sides in the width direction. The pair of snap fit structures 133a and 133b are displaced substantially equally to both sides in the width direction as the linear moving member 32G rises, and the linear moving member 32G passes between the locking parts 133c. In this way, the linear moving member 32G passes over the locking parts 133c of the pair of snap fit structures 133a and 133b, and pushing up of the staple S begins.

FIGS. 42 and 43 illustrate a state in which the ejection operation wire 6 has been further pulled by the operator.

As illustrated in FIGS. 42 and 43, if the operator further pulls the ejection operation wire 6, the first pulley 34 connected to the ejection operation wire 6 further rotates, and the linear moving member 32G is further pushed in the upward direction B1. The linear moving member 32G rises through the first through hole 134a formed between the pair of snap fit structures 133a and 133b and moves to an upper limit position thereof. When the linear moving member 32G is moved to the upper limit position, the pair of staples S are ejected from the storage housing 31G of the staple ejection part 3G. In this way, the treatment target T described above can be sutured by the staples S ejected from the staple ejection part 3.

According to the present embodiment, for example, even if a tension is applied to the ejection operation wire 6 due to curving deformation of the guide sheath, since the tension is equal to or less than a certain amount of pulling force (pulling force by the operator), a state in which the linear moving member 32G in contact with the pair of snap fit structures 133a and 133b is maintained, and it is possible to restrict an unintended rise of the linear moving member 32G. Thereby, it is possible to suppress the staple S being ejected at a timing not intended by the operator.

While embodiments of the present invention have been described in detail above with reference to the drawings, the specific configurations are not limited to the above-described embodiments, and may include design changes or the like within a range not departing from the gist of the present invention. Also, the components illustrated in the embodiments and modified examples described above can be configured by appropriately combining them.

INDUSTRIAL APPLICABILITY

The present invention can be applied to a medical stapler such as a stapler.

The invention claimed is:

1. A medical stapler, which is a medical stapler used together with an endoscope, comprising:
    a flexible elongated member extending in a length direction of the endoscope;
    a wire inserted inside the elongated member and movable forward and backward with respect to the elongated member;
    a suture assembly connected to a distal end of the wire and being able to suture a gripped treatment target with a staple;
    an operation unit connected to a rear end of the wire and ejecting the staple from the suture assembly by moving the wire forward and backward; and
    an ejection restriction structure restricting ejection of the staple when a tension applied to the wire is equal to or less than a first tension caused by a change in shape of the elongated member,
    wherein the ejection restriction structure includes a connector connecting the wire to the suture assembly and displaceable between a connection position with the suture assembly and a restriction position away from the connection position, and
    the connector is configured to be displaced from the restriction position to the connection position when the first tension is applied to the wire.

2. The medical stapler according to claim 1, wherein the ejection restriction structure has a function of releasing the ejection restriction of the staple when a tension equal to or more than a second tension, which is larger than the first tension, is applied to the wire by the operation unit.

3. The medical stapler according to claim 2, wherein the ejection restriction structure is provided in the suture assembly, and is configured to restrict movement of the staple when the tension applied to the wire is equal to or less than the second tension.

4. The medical stapler according to claim 3, wherein the ejection restriction structure is provided in the suture assembly and is displaceable between a restriction position for restricting movement of the staple and a release position for allowing movement of the staple, and the ejection restriction structure is configured to be disposed at the restriction position when the tension applied to the wire is equal to or less than the second tension, and to be displaced to the release position when the tension is equal to or more than the second tension.

5. The medical stapler according to claim 4, wherein the suture assembly includes:

a support member supporting the staple and movable in an ejection direction of the staple;

an extrusion member moving the support member in the ejection direction; and the ejection restriction structure lockable onto either the support member or the extrusion member at the restriction position.

6. The medical stapler according to claim 3, wherein the suture assembly includes:

a support member supporting the staple and movable in an ejection direction of the staple;

an extrusion member moving the support member in the ejection direction; and a rotation shaft supporting the extrusion member to be rotatable, and the ejection restriction structure is constituted by a high friction part provided between the rotation shaft and the extrusion member.

7. The medical stapler according to claim 2, wherein the ejection restriction structure is configured to impart a bend to the wire when the tension applied to the wire is equal to or less than the second tension.

8. The medical stapler according to claim 2, wherein the wire extends when a tension equal to or more than the first tension and equal to or less than the second tension is applied to the wire by the operation unit.

9. The medical stapler according to claim 1, wherein the suture assembly includes:

a first member ejecting the staple toward the treatment target by rotating; and a second member supporting the wire wound around the first member, and the second member is configured to be displaceable from a restriction position to a tension alleviation position when the first tension is applied to the wire.

* * * * *